(12) United States Patent
Zheng et al.

(10) Patent No.: US 11,702,412 B2
(45) Date of Patent: Jul. 18, 2023

(54) BICYCLIC [4,6,0] HYDROXAMIC ACIDS AS HDAC INHIBITORS

(71) Applicant: Valo Health, Inc., Boston, MA (US)

(72) Inventors: Xiaozhang Zheng, Lexington, MA (US); Pui Yee Ng, Lexington, MA (US); Aleksandra Rudnitskaya, Roslindale, MA (US); David R. Lancia, Jr., Boston, MA (US)

(73) Assignee: Valo Health, Inc., Boston, MA (US)

(*) Notice: Subject to any disclaimer, the term of this patent is extended or adjusted under 35 U.S.C. 154(b) by 125 days.

(21) Appl. No.: 17/124,778

(22) Filed: Dec. 17, 2020

(65) Prior Publication Data

US 2021/0206755 A1 Jul. 8, 2021

Related U.S. Application Data

(62) Division of application No. 16/522,082, filed on Jul. 25, 2019, now Pat. No. 10,870,645, which is a division of application No. 16/199,489, filed on Nov. 26, 2018, now Pat. No. 10,407,418, which is a division of application No. 15/013,811, filed on Feb. 2, 2016, now Pat. No. 10,183,934.

(60) Provisional application No. 62/110,719, filed on Feb. 2, 2015.

(51) Int. Cl.
| | | |
|---|---|---|
| C07D 267/22 | (2006.01) | |
| C07D 413/06 | (2006.01) | |
| C07D 498/04 | (2006.01) | |
| A61P 19/02 | (2006.01) | |
| A61P 25/28 | (2006.01) | |
| A61P 35/00 | (2006.01) | |

(52) U.S. Cl.
CPC ......... *C07D 413/06* (2013.01); *C07D 267/22* (2013.01)

(58) Field of Classification Search
CPC .. C07D 267/22; C07D 413/06; C07D 498/04; A61K 31/5545; A61P 19/02; A61P 25/28; A61P 35/00
See application file for complete search history.

(56) References Cited

U.S. PATENT DOCUMENTS

| | | |
|---|---|---|
| 4,332,802 A | 6/1982 | Schromm et al. |
| 4,861,784 A | 8/1989 | Rauber et al. |
| 5,153,185 A | 10/1992 | DiNinno et al. |
| 5,244,911 A | 9/1993 | Booher et al. |
| 5,294,610 A | 3/1994 | DiNinno et al. |
| 5,384,317 A | 1/1995 | DiNinno |
| 5,532,261 A | 7/1996 | DiNinno et al. |
| 5,612,356 A | 3/1997 | Yoshimura et al. |
| 5,714,518 A | 2/1998 | Reich et al. |
| 5,719,144 A | 2/1998 | Hartman et al. |
| 5,728,844 A | 3/1998 | Muller et al. |
| 5,807,854 A | 9/1998 | Bartroli et al. |
| 5,863,950 A | 1/1999 | Reich et al. |
| 6,001,823 A | 12/1999 | Hultgren et al. |
| 6,110,913 A | 8/2000 | Dorwald et al. |
| 6,153,396 A | 11/2000 | Hultgren et al. |
| 6,180,640 B1 | 1/2001 | Cuny et al. |
| 6,288,099 B1 | 9/2001 | Antane et al. |
| 6,403,632 B1 | 6/2002 | Duan et al. |
| 6,414,029 B1 | 7/2002 | Shechter et al. |
| 6,420,127 B1 | 7/2002 | Hultgren et al. |
| 6,476,019 B1 | 11/2002 | Radeke et al. |
| 6,762,177 B2 | 7/2004 | Radeke et al. |
| 6,787,554 B2 | 9/2004 | Gaudilliere |
| 6,872,542 B1 | 3/2005 | Hultgren et al. |
| 6,916,809 B2 | 7/2005 | Chen et al. |
| 6,962,791 B2 | 11/2005 | Hultgren et al. |
| 6,992,077 B2 | 1/2006 | Radeke et al. |

(Continued)

FOREIGN PATENT DOCUMENTS

| | | |
|---|---|---|
| CN | 101296910 A | 10/2008 |
| CN | 102558200 A | 7/2012 |

(Continued)

OTHER PUBLICATIONS

Aldana-Masangkay, G.I. and Sakamoto, K.M. The Role of HDAC6 in Cancer, J. Biomed. Biotechnol., 875824: 1-10 (2011).

(Continued)

*Primary Examiner* — Brenda L Coleman

(74) *Attorney, Agent, or Firm* — Choate, Hall & Stewart LLP; Michael A. Shinall; Nicholas J. Pace

(57) ABSTRACT

The present invention relates to inhibitors of zinc-dependent histone deacetylases (HDACs) useful in the treatment of diseases or disorders associated with HDAC6, having a Formulae I or Formula II:

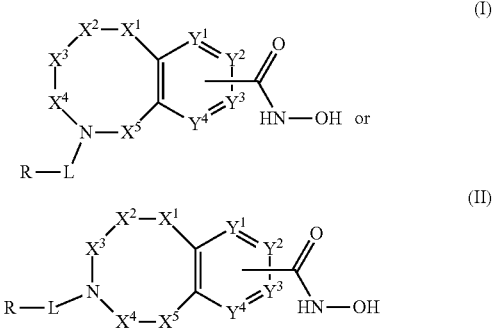

where R, L, $X^1$, $X^2$, $X^3$, $X^4$, $X^5$, $Y^1$, $Y^2$, $Y^3$, and $Y^4$ are described herein.

18 Claims, No Drawings

(56) References Cited

U.S. PATENT DOCUMENTS

| | | |
|---|---|---|
| 7,199,119 B2 | 4/2007 | Burkitt et al. |
| 7,214,690 B2 | 5/2007 | Higuchi et al. |
| 7,241,775 B2 | 7/2007 | Hofmeister et al. |
| 7,495,111 B2 | 2/2009 | Ramamoorthy et al. |
| 7,582,667 B2 | 9/2009 | Quagliato et al. |
| 7,622,582 B2 | 11/2009 | Kesteleyn et al. |
| 7,704,756 B2 | 4/2010 | Suich et al. |
| 7,705,017 B2 | 4/2010 | Cummings et al. |
| 7,723,349 B2 | 5/2010 | Yao et al. |
| 7,943,608 B2 | 5/2011 | Schultz et al. |
| 7,951,795 B2 | 5/2011 | Bell et al. |
| 8,058,427 B2 | 11/2011 | Hsieh et al. |
| 8,119,655 B2 | 2/2012 | Dong et al. |
| 8,148,380 B2 | 4/2012 | Guiles et al. |
| 8,178,553 B2 | 5/2012 | Lavey et al. |
| 8,198,290 B2 | 6/2012 | Hodges |
| 8,324,221 B2 | 12/2012 | Banka et al. |
| 8,349,839 B2 | 1/2013 | Sturino et al. |
| 8,367,709 B2 | 2/2013 | Pinto et al. |
| 8,426,447 B2 | 4/2013 | White et al. |
| 8,436,005 B2 | 5/2013 | Liu et al. |
| 8,471,026 B2 | 6/2013 | Blackburn et al. |
| 8,513,433 B2 | 8/2013 | Panicker et al. |
| 8,518,964 B2 | 8/2013 | Truchon et al. |
| 8,524,732 B2 | 9/2013 | Schiemann et al. |
| 8,546,410 B2 | 10/2013 | Liu et al. |
| 8,569,336 B2 | 10/2013 | Tong et al. |
| 8,575,193 B2 | 11/2013 | Maier et al. |
| 8,598,342 B2 | 12/2013 | Kahne et al. |
| 8,629,272 B2 | 1/2014 | Fuchs et al. |
| 8,642,587 B2 | 2/2014 | Lange et al. |
| 8,642,615 B2 | 2/2014 | Wentland |
| 8,658,641 B2 | 2/2014 | Barvian et al. |
| 8,673,952 B2 | 3/2014 | Blaquiere et al. |
| 8,685,969 B2 | 4/2014 | Liu et al. |
| 8,686,032 B2 | 4/2014 | Davidson et al. |
| 8,703,936 B2 | 4/2014 | Jewett et al. |
| 8,765,773 B2 | 7/2014 | England et al. |
| 8,765,810 B2 | 7/2014 | Greene et al. |
| 8,778,931 B2 | 7/2014 | Gould |
| 8,785,626 B2 | 7/2014 | Blaquiere et al. |
| 8,815,891 B2 | 8/2014 | Kim et al. |
| 8,822,462 B2 | 9/2014 | Traynelis et al. |
| 8,822,488 B2 | 9/2014 | Deaver et al. |
| 8,871,759 B2 | 10/2014 | Coburn et al. |
| 9,630,922 B2 | 4/2017 | Ng et al. |
| 9,637,453 B2 | 5/2017 | Ng et al. |
| 10,112,915 B2 | 10/2018 | Zheng et al. |
| 10,183,934 B2 | 1/2019 | Zheng et al. |
| 10,214,500 B2 | 2/2019 | Zheng et al. |
| 10,214,501 B2 | 2/2019 | Zheng et al. |
| 10,239,845 B2 | 3/2019 | Zheng et al. |
| 10,377,726 B2 | 8/2019 | Zheng et al. |
| 10,407,418 B2 | 9/2019 | Zheng et al. |
| 10,414,738 B2 | 9/2019 | Zheng et al. |
| 10,421,731 B2 | 9/2019 | Zheng et al. |
| 10,421,732 B2 | 9/2019 | Zheng et al. |
| 10,428,031 B2 | 10/2019 | Zheng et al. |
| 10,442,776 B2 | 10/2019 | Zheng et al. |
| 10,450,283 B2 | 10/2019 | Zheng et al. |
| 10,450,284 B2 | 10/2019 | Zheng et al. |
| 10,457,652 B2 | 10/2019 | Zheng et al. |
| 10,464,909 B2 | 11/2019 | Zheng et al. |
| 10,464,910 B2 | 11/2019 | Zheng et al. |
| 10,472,337 B2 | 11/2019 | Zheng et al. |
| 10,494,351 B2 | 12/2019 | Zheng et al. |
| 10,494,352 B2 | 12/2019 | Zheng et al. |
| 10,494,353 B2 | 12/2019 | Zheng et al. |
| 10,494,354 B2 | 12/2019 | Zheng et al. |
| 10,513,501 B2 | 12/2019 | Zheng et al. |
| 10,555,935 B2 | 2/2020 | Zheng et al. |
| 10,822,316 B2 | 11/2020 | Zheng et al. |
| 10,829,461 B2 | 11/2020 | Zheng et al. |
| 10,829,462 B2 | 11/2020 | Zheng et al. |
| 10,870,645 B2 | 12/2020 | Zheng et al. |
| 10,874,649 B2 | 12/2020 | Zheng et al. |
| 10,988,450 B2 | 4/2021 | Zheng et al. |
| 11,279,681 B2 | 3/2022 | Zheng et al. |
| 2002/0034774 A1 | 3/2002 | Hultgren et al. |
| 2002/0045199 A1 | 4/2002 | Hultgren et al. |
| 2003/0171355 A1 | 9/2003 | Radeke et al. |
| 2003/0198992 A1 | 10/2003 | Hultgren et al. |
| 2003/0208066 A1 | 11/2003 | Levin et al. |
| 2004/0249147 A1 | 12/2004 | Sattigeri et al. |
| 2005/0038011 A1 | 2/2005 | Radeke et al. |
| 2006/0069083 A1 | 3/2006 | Steiner et al. |
| 2006/0194785 A1 | 8/2006 | Radeke et al. |
| 2006/0239909 A1 | 10/2006 | Anderson et al. |
| 2007/0155730 A1 | 7/2007 | Leit et al. |
| 2007/0185007 A1 | 8/2007 | Jin et al. |
| 2007/0197564 A1 | 8/2007 | Lavey et al. |
| 2007/0244154 A1 | 10/2007 | Brehm |
| 2007/0265299 A1 | 11/2007 | Lavey et al. |
| 2008/0004282 A1 | 1/2008 | Vohra et al. |
| 2008/0112889 A1 | 5/2008 | Buggy et al. |
| 2008/0113962 A1 | 5/2008 | Zimmermann et al. |
| 2008/0194638 A1 | 8/2008 | Dedhiya et al. |
| 2008/0255161 A1 | 10/2008 | Koltun et al. |
| 2008/0275029 A1 | 11/2008 | Berdini et al. |
| 2008/0280855 A1 | 11/2008 | Chiesa et al. |
| 2009/0093473 A1 | 4/2009 | Zimmermann et al. |
| 2009/0105283 A1 | 4/2009 | Koltun et al. |
| 2009/0136449 A1 | 5/2009 | Di Filippo et al. |
| 2009/0156586 A1 | 6/2009 | Lavey et al. |
| 2009/0221589 A1 | 9/2009 | Trieselmann et al. |
| 2009/0325948 A1 | 12/2009 | Hurley et al. |
| 2010/0076012 A1 | 3/2010 | Schiemann et al. |
| 2010/0120818 A1 | 5/2010 | Enderle |
| 2010/0173332 A1 | 7/2010 | Smaill et al. |
| 2010/0256082 A1 | 10/2010 | Schotzinger |
| 2010/0317678 A1 | 12/2010 | Moffat et al. |
| 2011/0039827 A1 | 2/2011 | Blackburn et al. |
| 2011/0039840 A1 | 2/2011 | Varasi et al. |
| 2011/0071136 A1 | 3/2011 | Haddach et al. |
| 2011/0076292 A1 | 3/2011 | Blaguiere et al. |
| 2011/0098267 A1 | 4/2011 | Babu et al. |
| 2011/0251184 A1 | 10/2011 | Blackburn et al. |
| 2011/0275762 A1 | 11/2011 | Cmiljanovic et al. |
| 2011/0288117 A1 | 11/2011 | Gould et al. |
| 2012/0015942 A1 | 1/2012 | Calderwood et al. |
| 2012/0015943 A1 | 1/2012 | Blackburn et al. |
| 2012/0083483 A1 | 4/2012 | Coburn et al. |
| 2012/0094997 A1 | 4/2012 | England et al. |
| 2012/0121502 A1 | 5/2012 | Van Duzer et al. |
| 2012/0165316 A1 | 6/2012 | Gould |
| 2012/0244149 A1 | 9/2012 | Blaguiere et al. |
| 2012/0245144 A1 | 9/2012 | Heffron et al. |
| 2012/0245193 A1 | 9/2012 | Silverman et al. |
| 2012/0258949 A1 | 10/2012 | Varasi et al. |
| 2013/0029938 A1 | 1/2013 | Aquino et al. |
| 2013/0079331 A1 | 3/2013 | Blaguiere et al. |
| 2013/0281402 A1 | 10/2013 | Chen et al. |
| 2013/0289027 A1 | 10/2013 | De La Rosa et al. |
| 2013/0303567 A1 | 11/2013 | Panicker et al. |
| 2014/0018343 A1 | 1/2014 | Romero et al. |
| 2014/0018361 A1 | 1/2014 | Harriman et al. |
| 2014/0031302 A1 | 1/2014 | Winssinger et al. |
| 2014/0031340 A1 | 1/2014 | Dineen et al. |
| 2014/0038954 A1 | 2/2014 | Epstein et al. |
| 2014/0088101 A1 | 3/2014 | Ng et al. |
| 2014/0128371 A1 | 5/2014 | Barvian et al. |
| 2014/0194386 A1 | 7/2014 | Burns et al. |
| 2014/0239288 A1 | 8/2014 | Delcamp et al. |
| 2014/0241990 A1 | 8/2014 | Haydon et al. |
| 2014/0288047 A1 | 9/2014 | Blaguiere et al. |
| 2014/0296226 A1 | 10/2014 | White et al. |
| 2014/0323447 A1 | 10/2014 | Kley et al. |
| 2016/0221972 A1 | 8/2016 | Zheng et al. |
| 2016/0221973 A1 | 8/2016 | Zheng et al. |
| 2016/0221997 A1 | 8/2016 | Zheng et al. |
| 2016/0222022 A1 | 8/2016 | Zheng et al. |
| 2016/0222028 A1 | 8/2016 | Zheng et al. |
| 2016/0304456 A1 | 10/2016 | Ng et al. |
| 2016/0304462 A1 | 10/2016 | Ng et al. |

(56) References Cited

U.S. PATENT DOCUMENTS

| | | |
|---|---|---|
| 2019/0016692 A1 | 1/2019 | Zheng et al. |
| 2019/0016693 A1 | 1/2019 | Zheng et al. |
| 2019/0062288 A1 | 2/2019 | Zheng et al. |
| 2019/0092762 A1 | 3/2019 | Zheng et al. |
| 2019/0112279 A1 | 4/2019 | Zheng et al. |
| 2019/0112280 A1 | 4/2019 | Zheng et al. |
| 2019/0112281 A1 | 4/2019 | Zheng et al. |
| 2019/0112282 A1 | 4/2019 | Zheng et al. |
| 2019/0112283 A1 | 4/2019 | Zheng et al. |
| 2019/0112284 A1 | 4/2019 | Zheng et al. |
| 2019/0119227 A1 | 4/2019 | Zheng et al. |
| 2019/0119228 A1 | 4/2019 | Zheng et al. |
| 2019/0119229 A1 | 4/2019 | Zheng et al. |
| 2019/0119230 A1 | 4/2019 | Zheng et al. |
| 2019/0119231 A1 | 4/2019 | Zheng et al. |
| 2019/0119232 A1 | 4/2019 | Zheng et al. |
| 2019/0119233 A1 | 4/2019 | Zheng et al. |
| 2019/0119234 A1 | 4/2019 | Zheng et al. |
| 2019/0119235 A1 | 4/2019 | Zheng et al. |
| 2019/0127339 A1 | 5/2019 | Zheng et al. |
| 2019/0201384 A1 | 7/2019 | Zheng et al. |
| 2019/0345149 A1 | 11/2019 | Zheng et al. |
| 2020/0002298 A1 | 1/2020 | Zheng et al. |
| 2020/0048211 A1 | 2/2020 | Zheng et al. |
| 2020/0048212 A1 | 2/2020 | Zheng et al. |
| 2020/0055830 A1 | 2/2020 | Zheng et al. |
| 2020/0121655 A1 | 4/2020 | Zheng et al. |
| 2021/0009538 A1 | 1/2021 | Zheng et al. |
| 2021/0009539 A1 | 1/2021 | Zheng et al. |
| 2021/0009540 A1 | 1/2021 | Zheng et al. |
| 2021/0186940 A1 | 6/2021 | Zheng et al. |
| 2022/0204461 A1 | 6/2022 | Zheng et al. |
| 2022/0363651 A1 | 11/2022 | Zheng et al. |

FOREIGN PATENT DOCUMENTS

| | | |
|---|---|---|
| CN | 102838625 A | 12/2012 |
| EP | 2110377 A1 | 10/2009 |
| GB | 2503789 A | 1/2014 |
| JP | 2000/044562 A | 2/2000 |
| JP | 2000/357809 A | 12/2000 |
| JP | 2001/226269 A | 8/2001 |
| JP | 2004/210716 A | 7/2004 |
| JP | 4162106 B2 | 10/2008 |
| JP | 2009-509923 A | 3/2009 |
| JP | 2009/191041 A | 8/2009 |
| JP | 2011-148714 A | 8/2011 |
| JP | 2012-530703 A | 12/2012 |
| WO | WO-9503699 A1 | 2/1995 |
| WO | WO-9514028 A2 | 5/1995 |
| WO | WO-9748786 A1 | 12/1997 |
| WO | WO-9901607 A2 | 1/1999 |
| WO | WO-9967238 A2 | 12/1999 |
| WO | WO-2000/034285 A2 | 6/2000 |
| WO | WO-01/12630 A1 | 2/2001 |
| WO | WO-2002/036066 A2 | 5/2002 |
| WO | WO-2002/042273 A2 | 5/2002 |
| WO | WO-2003/087059 A2 | 10/2003 |
| WO | WO-2004/017950 A2 | 3/2004 |
| WO | WO-2004/056182 A1 | 7/2004 |
| WO | WO-2004/063156 A1 | 7/2004 |
| WO | WO-2004/111052 A1 | 12/2004 |
| WO | WO-2005/108367 A1 | 11/2005 |
| WO | WO-2005/123089 A2 | 12/2005 |
| WO | WO-2006/065842 A2 | 6/2006 |
| WO | WO-2006/083869 A2 | 8/2006 |
| WO | WO-2006/102557 A2 | 9/2006 |
| WO | WO-2006/138549 A1 | 12/2006 |
| WO | WO-2007/022638 A1 | 3/2007 |
| WO | WO-2007/023135 A1 | 3/2007 |
| WO | WO-2007/029035 A2 | 3/2007 |
| WO | WO-2007/061880 A1 | 5/2007 |
| WO | WO-2007/079826 A1 | 7/2007 |
| WO | WO-2007/084451 A1 | 7/2007 |
| WO | WO-2007/100536 A1 | 9/2007 |
| WO | WO-2007/109178 A2 | 9/2007 |
| WO | WO-2007/143822 A1 | 12/2007 |
| WO | WO-2008/011805 A1 | 1/2008 |
| WO | WO-2008/046155 A1 | 4/2008 |
| WO | WO-2008/048648 A2 | 4/2008 |
| WO | WO-2008/055068 A2 | 5/2008 |
| WO | WO-2008/060721 A1 | 5/2008 |
| WO | WO-2008/061160 A1 | 5/2008 |
| WO | WO-2008/071765 A1 | 6/2008 |
| WO | WO-2008/074858 A1 | 6/2008 |
| WO | WO-2008/091349 A1 | 7/2008 |
| WO | WO-2008/101186 A1 | 8/2008 |
| WO | WO-2009/100045 A1 | 8/2009 |
| WO | WO-2009/123967 A1 | 10/2009 |
| WO | WO-2009127609 A1 | 10/2009 |
| WO | WO-2009/137503 A1 | 11/2009 |
| WO | WO-2010/028192 A1 | 3/2010 |
| WO | WO-2010/042475 A1 | 4/2010 |
| WO | WO-2010/043893 A1 | 4/2010 |
| WO | WO-2010/054278 A2 | 5/2010 |
| WO | WO-2010/056230 A1 | 5/2010 |
| WO | WO-2010/092181 A1 | 8/2010 |
| WO | WO-2010/111483 A1 | 9/2010 |
| WO | WO-2010/125469 A1 | 11/2010 |
| WO | WO-2010/151317 A1 | 12/2010 |
| WO | WO-2010/151318 A1 | 12/2010 |
| WO | WO-2010/151441 A1 | 12/2010 |
| WO | WO-2011/002520 A2 | 1/2011 |
| WO | WO-2011/011186 A2 | 1/2011 |
| WO | WO-2011/036280 A1 | 3/2011 |
| WO | WO-2011/039353 A1 | 4/2011 |
| WO | WO-2011/045265 A2 | 4/2011 |
| WO | WO-2011/079036 A1 | 6/2011 |
| WO | WO-2011/084991 A2 | 7/2011 |
| WO | WO-2011/088181 A1 | 7/2011 |
| WO | WO-2011/091213 A2 | 7/2011 |
| WO | WO-2011/106627 A1 | 9/2011 |
| WO | WO-2011/106632 A1 | 9/2011 |
| WO | WO-2011/137135 A1 | 11/2011 |
| WO | WO-2011/146591 A1 | 11/2011 |
| WO | WO-2012/016081 A2 | 2/2012 |
| WO | WO-2012/027564 A1 | 3/2012 |
| WO | WO-2012/031993 A1 | 3/2012 |
| WO | WO-2012/045194 A1 | 4/2012 |
| WO | WO-2012/045804 A1 | 4/2012 |
| WO | WO-2012/054332 A1 | 4/2012 |
| WO | WO-2012/085003 A1 | 6/2012 |
| WO | WO-2012/088015 A2 | 6/2012 |
| WO | WO-2012/106343 A2 | 8/2012 |
| WO | WO-2012/110860 A1 | 8/2012 |
| WO | WO-2012/117421 A1 | 9/2012 |
| WO | WO-2012/126901 A1 | 9/2012 |
| WO | WO-2012/178208 A2 | 12/2012 |
| WO | WO-2013/006408 A1 | 1/2013 |
| WO | WO-2013/008162 A1 | 1/2013 |
| WO | WO-2013/009827 A1 | 1/2013 |
| WO | WO-2013/013113 A2 | 1/2013 |
| WO | WO-2013/033085 A1 | 3/2013 |
| WO | WO-2013/052110 A1 | 4/2013 |
| WO | WO-2013/059582 A2 | 4/2013 |
| WO | WO-2013/090210 A1 | 6/2013 |
| WO | WO-2013/134467 A1 | 9/2013 |
| WO | WO-2014/011753 A2 | 1/2014 |
| WO | WO-2014/018919 A1 | 1/2014 |
| WO | WO-2014/037342 A1 | 3/2014 |
| WO | WO-2014/048945 A1 | 4/2014 |
| WO | WO-2014/110442 A1 | 7/2014 |
| WO | WO-2014/127881 A1 | 8/2014 |
| WO | WO-2014/134127 A1 | 9/2014 |
| WO | WO-2014/178606 A1 | 11/2014 |
| WO | WO-2015/054474 A1 | 4/2015 |
| WO | WO-2015/137750 A1 | 9/2015 |
| WO | WO-2016/126721 A1 | 8/2016 |
| WO | WO-2016/126722 A1 | 8/2016 |
| WO | WO-2016/126724 A1 | 8/2016 |
| WO | WO-2016/126725 A1 | 8/2016 |
| WO | WO-2016/126726 A1 | 8/2016 |
| WO | WO-2016/168598 A1 | 10/2016 |

(56) References Cited

FOREIGN PATENT DOCUMENTS

| WO | WO-2016/168660 A1 | 10/2016 |
| WO | WO-2017/065473 A1 | 4/2017 |
| WO | WO-2017/218950 A1 | 12/2017 |

OTHER PUBLICATIONS

Amengual. J.E. et al, Dual Targeting of Protein Degradation Pathways with the Selective HDAC6 Inhibitor ACY-1215 and Bortezomib Is Synergistic in Lymphoma, Clin Cancer Res., 21(20):4663-75 (2015).
Bantscheff, M. et al., Chemoproteomics profiling of HDAC inhibitors reveal selective targeting of HDAC complexes, Nature Biotechnology, 29(3):255-265 (2011). Online Methods appended.
Bazzaro M. et al, Ubiquitin Proteasome System Stress Underlies Synergistic Killing of Ovarian Cancer Cells by Bortezomib and a Novel HDAC6 Inhibitor, Clin. Cancer Res., 14(22):7340-7347 (2008).
Benedetti R, Conte M, Altucci L. "Targeting Histone Deacetylases in Diseases: Where Are We?" Antioxidants & Redox Signaling, 23(1), pp. 99-126, 2015.
Bergman, J.A. et al., Selective histone deacetylase 6 inhibitors bearing substituted urea linkers inhibit melanoma cell growth, J. Med. Chem., 55:9891-9899 (2012).
Blackburn, C. et al., Histone deacetylase inhibitors derived from 1,2,3,4-tetrahydropyrrolo[1,2-a]pyrazine and related heterocycles selective for the HDAC6 isoform, Bioorg Med Chem Lett., 24(23):5450-5454 (2014).
Blackburn, C. et al., Potent Histone Deacetylase Inhibitors Derived from 4-(Aminomethyl)-N-hydroxybenzamide with High Selectivity for the HDAC6 Isoform, J Medicinal Chemistry, 56(18):7201-7211 (2013).
Bone, E.A. et al., Design and Development of HDAC6-Selective Inhibitors for Hematological Cancer Treatment and Solid Tumor Immunotherapy, Karus Therapeutics, Poster session presented at the AACR Annual Meeting, Philadelphia, PA, 1 page (2015). Abstract 3662.
Bradner, J.E. et al., Chemical phylogenetics of histone deacetylases, Nature Chemical Biology, 6:238-243 (2010). Supplemental Information appended, 26 pages.
Butler, K.V. and Kozikowski, A.P., Chemical Origins of Isoform Selectivity in Histone Deacetylase Inhibitors, Current Pharmaceutical Design, 14:505-528 (2008).
Butler, K.V. et al., Rational Design and Simple Chemistry Yield a Superior Neuroprotective HDAC6 Inhibitor, Tubastatin A, J. Am. Chem. Soc., 132:10842-10846 (2010).
Cancer, MedlinePlus, 10 pages. URL: http://www.nlm.nih.gov/medlineplus/cancer.html. [Retrieved Jul. 6, 2007].
Canet, E. and Touchon, P., Servier: Looking to the Future—Innovation-Driven Partnerships. Medicographia 120, vol. 36(3):267-429 (2014).
Cha, T.L. et al, Dual degradation of aurora A and B kinases by the histone deacetylase inhibitor LBH589 induces G2-M arrest and apoptosis of renal cancer cells, Clin. Cancer Res., 15(3): 840-850 (2009).
Choi, E. et al., Property-Based Optimization of Hydrozamate-Based γ-Lactam HDAC Inhibitors to Improve Their Metabolic Stability and Pharmacokinetic, J. Med. Chem., 55:10766-10770 (2012).
Choi, S.Y. et al, Tubastatin A suppresses renal fibrosis via regulation of epigenetic histone modification and Smad3-dependent fibrotic genes, Vascul. Pharmacol., 72:130-140 (2015).
Choi, Y., Anti-Multiple Myeloma Activity of a Novel HDAC6 Inhibitor, DC-004, in Combination with Proteosomal Inhibitors, CKD Pharmaceutical Corporation, Presentation at the DOT Meeting, 26 pages, Sep. 24, 2015.
Chuang, M.J. et al., The HDAC Inhibitor LBH589 Induces ERK-Dependent Prometaphase Arrest in Prostate Cancer via HDAC6 Inactivation and Down-Regulation, PLOS One, 8(9):e73401 (2013).

Dallavalle S, Pisano C, Zunino F. "Development and therapeutic impact of HDAC6-selective inhibitors",Biochemical Pharmacology, Sep. 15, 2012; 84(6):756-65.
De Ruijter, A.J. et al, Histone deacetylases (HDACs): characterization of the classical HDAC family, Biochem. J., 370: 737-749 (2003).
Dhakal, B.K. and Mulve, M.A., Uropathogenic *Escherichia coli* invades host cells via an HDAC6-modulated microtubule-dependent pathway, J. Biol. Chem., 284(1):446-454 (2008).
Di Micco, S. et al., Structural basis for the design and synthesis of selective HDAC inhibitors, Bioorganic & Medicinal Chemistry, 21:3795-3807 (2013).
Ding, G. et al, HDAC6 promotes hepatocellular carcinoma progression by inhibiting P53 transcriptional activity, FEBS Lett., 587:880-6 (2013).
Ding, N. et al, Histone deacetylase 6 activity is critical for the metastasis of Burkitt's lymphoma cells, Cancer Cell Int., 14:139 (2014).
D'Ydewalle, C. et al., HDAC6 inhibitors reverse axonal loss in a mouse model of mutant HSPB1-induced Charcot-Marie-Tooth disease, Nature Medicine, 8(17):968-974 (2011). Online Methods appended, 1 page.
Falkenberg, K.J. and Johnstone, R.W., Histone deacetylases and their inhibitors in cancer, neurological diseases and immune disorders, Nature Reviews, 13:673-691 (2014).
Feng, T. et al., Novel N-hydrozyfurylacrylamide-based histone deacetylase (HDAC) inhibitors with branched CAP group (Part 2), Bioorg. Med. Chem., 21(17):5339-5354 (2013).
Fiskus, W. et al, Molecular and biologic characterization and drug sensitivity of pan-histone deacetylase inhibitor-resistant acute myeloid leukemia cells, Blood, 112(7):2896-2905 (2008).
Golub et al., Molecular Classification of Cancer: Class Discovery and Class Prediction by Gene Expression Monitoring, Science (1999), vol. 286, 531-537.
Gupta, P. et al., Towards Isozyme-Selective HDAC Inhibitors For Interrogating Disease, Current Topics in Medicinal Chemistry, 12:1479-1499 (2012).
Haakenson, J. and Zhang, X., HDAC6 and Ovarian Cancer, Int. J. Mol. Sci., 14:9514-9535 (2013).
Hadley, M. et al., In Vivo Evaluation of Ames Negative HDAC6 Inhibitor in Melanoma Model. The George Washington Cancer Center. AACR Annual Meeting, Presentation Poster (2017).
Hahnen, E. et al., Histone deacetylase inhibitors: possible implications for neurodegenerative disorders, Expert Opin. Investig. Drugs, 17(2):1-16 (2008).
Hajiagha Bozorgi, A. et al., A structure-activity relationship survey of histone deacetylase (HDAC) inhibitors, Chemometrics and Intelligent Laboratory Systems, 125:132-138 (2013).
Hanessian, S. et al., Vorinostat-Like Molecules as Structural, Stereochemical, and Pharmacological Tools, ACS Med. Chem. Lett., 1:70-74 (2010).
Hideshima, T. et al, Small-molecule inhibition of proteasome and aggresome function induces synergistic antitumor activity in multiple myelomaProc. Natl. Acad. Sci. USA, 102(24):8567-8572 (2005).
Holson, E., Design of inter-class selective inhibitors and discovery of endogenous "HDAC" substrates, The Stanley Center for Psychiatric Research, The Board Institute of Harvard and MIT, Presentation at the DOT Meeting in Boston, 44 pages, Oct. 7, 2014.
Inks, E.S. et al., A Novel Class of Small Molecule Inhibitors of HDAC6, ACS Chem. Biol., 7:331-339 (2012).
International Search Report for PCT/US2016/016194, 4 pages (dated Mar. 23, 2016).
International Search Report for PCT/US2016/016197, 4 pages (dated Mar. 22, 2016).
International Search Report for PCT/US2016/016200, 4 pages (dated Mar. 22, 2016).
International Search Report for PCT/US2016/016201, 4 pages (dated Apr. 20, 2016).
International Search Report for PCT/US2016/016204, 4 pages (dated Mar. 22, 2016).
International Search Report for PCT/US2016/027755, 8 pages (dated Aug. 23, 2016).

(56) References Cited

OTHER PUBLICATIONS

International Search Report for PCT/US2016/027842, 8 pages (dated Aug. 12, 2016).
International Search Report for PCT/US2017/037970, 5 pages (dated Aug. 9, 2017).
Itoh, Y. et al., Design, Synthesis, Structure—Selectivity Relationship, and Effect on Human Cancer Cells of a Novel Series of Histone Deacetylase 6-Selective Inhibitors, J. Med. Chem., 50:5425-5438 (2007).
Jochems, J. et al., Antidepressant-Like Properties of Novel HDAC6-Selective Inhibitors with Improved Brain Bioavailability, Neuropsychopharmacology, 39:389-400 (2014).
Kalin JH, Bergman JA. "Development and therapeutic implications of selective histone deacetylase 6 inhibitors", J Med Chem. Aug. 22, 2013; 56(16):6297-313.
Kalin, J.H. et al, Second-generation histone deacetylase 6 inhibitors enhance the immunosuppressive effects of Foxp3+ T-regulatory cells, J. Med. Chem., 55:639-651 (2012).
Kaliszczak, M. et al., A novel small molecule hydroxamate preferentially inhibits HDAC6 activity and tumour growth, British Journal of Cancer, 108:342-350 (2013).
Kamemura, K. et al, Effects of downregulated HDAC6 expression on the proliferation of lung cancer cells, Biochem. Biophys. Res. Commun., 374(1):84-89 (2008).
Kanno, K. et al, Overexpression of histone deacetylase 6 contributes to accelerated migration and invasion activity of hepatocellular carcinoma cells, Oncol. Rep., 28: 867-73 (2012).
Katharaj, E. and Jayaraman, R., Histone Deacetylase Inhibitors as Therapeutics Agents for Cancer Therapy: Drug Metabolism and Pharmacokinetic Propoerties, Drug Development—A Case Study Based Insight into Modern Strategies, InTech, 21 pages (2011).
Kee, H.J. et al., HDAC Inhibition Suppresses Cardiac Hypertrophy and Fibrosis in DOCA-Salt Hypertensive Rats via Regulation of HDAC6/HDAC8 Enzyme Activity, 37(4-5):229-239 (2013).
Kim, H.J. and Bae, S.C., Histone deacetylase inhibitors: molecular mechanisms of action and clinical trials as anti-cancer drugs, Am J Transl Res, 3(2):166-179 (2011).
Kim, J. et al., A Novel Regulatory Role of HDAC6 in the Functional Inflammatory Phenotype of Glia cells. The George Washington University Cancer Center. AACR Annual Meeting, Presentation Poster (2017).
Kim, Y.H. et al., A phase 1b Study in Cutaneous T-cell lymphoma (CTCL) with the novel topically applied skin-restricted histone deacetylase inhibitor (HDAC-i) SHP-141. Journal of Clinical Oncology 32:15_suppl, 8525-8525 (2014).
Konsoula, Z. et al., Pharmacokinetics-pharmacodynamics and antitumor activity of mercaptoacetamide-based histone deacetylase inhibitors, Mol Cancer Ther, 8(10):2844-2851 (2009).
Kozikowski, A.P. et al., Use of the Nitrile Oxide Cycloaddition (NOC) Reaction for Molecular Probe Generation: A New Class of Enzyme Selective Histone Deacetylase Inhibitors (HDACIs) Showing Picomolar Activity of HDAC6, J. Med. Chem., 51:4370-4373 (2008).
Kozikowski, A.P., Chemistry, the Brain, and Cancer—Ups and Downs on the Road to HDAC Drugs, Department of Medicinal Chemistry and Pharmacognosy, University of Illinois at Chicago, 61 pages, 2017.
Kroesen, K. et al., HDAC inhibitors and immunotherapy; a double edged sword?, Oncotarget, 5(16):6558-6572 (2014).
Krukowski, K. et al., Abstract 1612: An HDAC6 inhibitor for treatment of chemoterapy-induced peripheral numbness and pain in a mouse model, Abstracts/Brain, Behavior, and Immunity, 49:e28 (2015).
Kwon, S.H., Selective Inhibition of HDAC6 regulates preferential cytotoxicity in cancer cells by modulating p53 and Hsp90 stability, American Association for Cancer Research Annual Meeting, Philadelphia, Abstract 5324, 16 pages (Apr. 22, 2015).
Lai, M.J. et al., Synthesis and Biological Evaluation of 1-Arylsulfonyl-5-(N-hydroxyacrylamide)indoles as Potent Histone Deacetylase Inhibitors with Antitumor Activity in Vivo, J. Med. Chem., 55:3777-3791 (2012).
Lala et al., Role of nitric oxide in tumor progression: Lessons from experimental tumors, Cancer and Metastasis Reviews (1998), 17, 91-106.
Lee, J. and Huang, S.R., Cancer Epigenetics: Mechanisms and Crosstalk of HDAC Inhibitor, Vorinostat, Chemotherapy, 2(1):1000111 (2013).
Lee, J.H. et al., Anti-Multiple Myeloma Activity of a Novel HDAC6 Inhibitor, DC-004, in Combination with Proteosomal Inhibitors. CKD Research Institute (2015).
Lee, J.H. et al., Development of a histone deacetylase 6 inhibitor and its biological effects, PNAS Early Edition, 110(39):15704-15709 (2013).
Lee, Y-S. et al, The cytoplasmic deacetylase HDAC6 is required for efficient oncogenic tumorigenesisCancer Res., 68(18):7561-7569 (2008).
Li, Y. et al, Histone deacetylase 6 plays a role as a distinct regulator of diverse cellular processes, FEBS J., 280: 775-93 (2013).
Lim, H. et al., CKD-M134, a Novel HDAC6 Inhibitor, Ameliorates Experimental Colitis Models in Mice. CKD Research Institute, Presentation Poster, 1 page (Sep. 25, 2015).
Lin, X. et al., Design and Synthesis of Orally Bioavailable Aminopyrrolidinone Histone Deacetylase 6 Inhibitors, J. Med. Chem., 58:2809-2820 (2015).
Marek, L. et al., Histone Deacetylase (HDAC) Inhibitors with a Novel Connecting Unit Linker Region Reveal a Selectivity Profile for HDAC4 and HDAC5 with Improved Activity against Chemoresistant Cancer Cells, J. Med. Chem., 56(2):427-436 (2013).
Marek, M. et al. Structural basis for the inhibition of histone deacetylase 8 (HDAC8), a key epigenetic player in the blood fluke Schistosoma mansoni, PLoS Pathog. 9(9): 1-15, e1003645 (2013).
Mishima, Y. et al., Ricolinostat (ACY-1215) induced inhibition of aggresome formation accelerates carfilzomib-induced multiple myeloma cell death, British Journal of Haematology, 169(9):423-434 (2015).
Molina, A. et al., Identification of ACY-1083: a Novel, Potent, and Highly Selective HDAC6 Inhibitor, Acetylon Pharmaceuticals, Inc., Poster presentation, 1 page, 2016.
Mottamal, M. et al., Histone Deacetylase Inhibitors in Clinical Studies as Templates for New Anticancer Agents, Molecules, 20:3898-3941 (2015).
Nawrocki, S.T. et al, Aggresome disruption: a novel strategy to enhance bortezomib-induced apoptosis in pancreatic cancer cells, Cancer Res., 66(7):3773-3781 (2006).
New, M. et al., HDAC inhibitor-based therapies: Can we interpret the code?, Molecular Oncology, 6:637-656 (2012).
Olson, D.E. et al., Discovery of the First Histone Deacetylase 6/8 Dual Inhibitors, J. Med. Chem., 56:4816-4820 (2013).
Park, S.Y. et al, Histone deacetylases 1, 6 and 8 are critical for invasion in breast cancer, Oncol. Rep. 2011, 25: 1677-1681 (2011).
Quartararo, C.E. et al., High-Throughput Screening of Patient-Derived Cultures Reveals Potential for Precision Medicine in Glioblastoma, ASC Med. Chem. Lett., 6:948-952 (2015).
Quayle, S.N. et al., Selective HDAC Inhibition by Ricolinostat (ACY-1215) or ACY-241 Synergizes with IMiD® Immunomodulatory Drugs in Multiple Myeloma (MM) and Mantle Cell Lymphoma (MCL) Cells, Acetylon Pharmaceuticals, Inc., AACR Poster Presentation in Boston, MA, 1 page (2015).
Raje, N. et al., Ricolinostat plus Lenalidomide and Dexamethasone in Patients with Relapsed & Refractory Multiple Myeloma: Phase 1B & Early Phase 2 Results, Acetylon Pharamceuticals Inc, Poster Presentation (2015).
Rey, M. et al., HDAC6 is required for invadopodia activity and invasion by breast tumor cells, Eur. J. Cell Biol., 90: 128-135 (2011).
Rivieccio, M.A. et al, HDAC6 is a target for protection and regeneration following injury in the nervous system, Proc. Natl. Acad. Sci. USA, 106(46):19599-195604 (2009).
Rodriguez-Gonzalez, R. et al, Multiple system organ response induced by hyperoxia in a clinically relevant animal model of sepsis, Blood 2008, 1 12(1 1): Abstract 1923 (2008).

(56) References Cited

OTHER PUBLICATIONS

Seidel, C. et al, 4-Hydroxybenzoic acid derivatives as HDAC6-specific inhibitors modulating microtubular structure and HSP90a chaperone activity against prostate cancer, Biochem. Pharmacol., 99: 31-52 (2016).

Seki, H. et al., Synthesis/biological evaluation of hydrozamic acids and their prodrugs as inhibitors for Botulinum neurotoxin A light chain, Bioorganic & Medicinal Chemistry, 22:1208-1217 (2014).

Shen, S. et al., Bicyclic-Capped Histone Deacetylase 6 Inhibitors with Improved Activity in a Model of Axonal Charcot-Marie-Tooth Disease, ACS Chem Neurosci., 7(2):240-258 (2016).
Shon, S. et al., Abstract 1448: Therapeutic Role of a Novel Histone Deacetylase 6 Inhibitor, CKD-M808, in Rheumatoid Arthritis, ACR/ARHP Annual Meeting, 2 pages (2016). Accessed May 25, 2018. <http://acrabstracts.org/abstract/therapeutic-role-of-a-novel-histone-deacetylase-6-inhibitor-ckd-m808-in-rheumatoid-arthritis/>.
Simoes-Pires, C. et al, HDAC6 as a target for neurodegenerative diseases: what makes it different from the other HDACs?, Mol. Neurodegener., 8: 7 (2013).
Suzuki, T. et al., Highly Potent and Selective Histone Deacetylase 6 Inhibitors Designed Based on a Small-Molecular Substrate, J. Med. Chem., 49:4809-4812 (2006).
Tang J, Yan H, Zhuang S. "Histone deacetylases as targets for treatment of multiple diseases", Clinical Science (Lond), Jun. 2013; 124(11):651-62.
Tang, G. et al., Identification of a Novel Aminotetralin Class of HDAC6 and HDAC8 Selective Inhibitors, J. Med. Chem., 57(19):8026-8034 (2014).
Tannous, P. et al, Intracellular protein aggregation is a proximal trigger of cardiomyocyte autophagy, Circulation, 117(24):3070-3078 (2008).
Tapadar, S. et al., Isoxazole moiety in the linker region of HDAC inhibitors adjacent to the Zn-chelating group: Effects on HDAC biology and antiproliferative activity, Bioorganic & Medicinal Chemistry Letters, 19:3023-3026 (2009).
Thaler, F. et al., Current trends in the development of histone deacetylase inhibitors: a review of recent patent applications, Pharm. Pat. Analyst, 1(1):75-90 (2012).
Thangapandian, S. et al., Molecular Modeling Study on Tunnel Behavior in Different Histone Deacetylase Isoforms, Plos One, 7(11):e49327 (2012).
Valente, S. and Mai, A., Small-molecule inhibitors of histone deacetylase for the treatment of cancer and non-cancer diseases: a patent review (2011-2013), Expert Opin. Ther. Patents, 24(4):401-415 (2014).
Van Helleputte, L. et al., The role of histone deacetylase 6 (HDAC6) in neurodegeneration, Research and Reports in Biology, 5:1-13 (2014).
Varasi, M. et al., Discovery, Synthesis, and Pharmacological Evaluation of Spiropiperidine Hydroxamic Acid Based Derivatives as Structurally Novel Histone Deacetylase (HDAC) Inhibitors, Journal of Medicinal Chemistry, 54(8): 3051-3064 (2011).
Vishwakarma, S. et al, Tubastatin, a selective histone deacetylase 6 inhibitor shows anti-inflammatory and anti-rheumatic effects, Int. Immunopharmacol., 16:72-78 (2013).
Wagner, F.F. et al., Potent and Selective Inhibition of Histone Deacetylase 6 (HDAC6) Does Not Require a Surface-Binding Motif, J. Med. Chem., 56:1772-1776 (2013).
Wagner, F.F. et al., Small Molecule Inhibitors of Zinc-dependent Histone Deacetylases, Neurotherapeutics, 10(4):589-604 (2013).
Wang, L. et al, Immunomodulatory effects of deacetylase inhibitors: therapeutic targeting of FOXP3+ regulatory T cellsNat. Rev. Drug Disc. 2009 8(12):969-981.
Wang, Z. et al., HDAC6 promotes cell proliferation and confers resistance to temozolomide in glioblastoma. Cancer Letters 379:134-142 (2016).
West AC, Johnstone RW, "New and emerging HDAC inhibitors for cancer treatment", Journal of Clinical Investigation, Jan. 2, 2014; 124(1):30-9.
Wu, D. et al., Screening of selective histone deacetylase inhibitors by proteochemometric modeling, BMC Bioinformatics, 13:212 (2012).
Yang, M.H. et al., HDAC6 and SIRT2 regulate the acetylation state and oncogenic activity of mutant K-RAS, Mol Cancer Res, 11(9):1072-1077 (2013).
Yu, C.W. et al., Quinazolin-4-one Derivatives as Selective Histone Deacetylase-6 Inhibitors for the Treatment of Alzheimer's Disease, J. Med. Chem., 56(17):6775-6791 (2013).
Zhang, L. et al, Proteomic identification and functional characterization of MYH9, Hsc70, and DNAJA1 as novel substrates of HDAC6 deacetylase activity, Protein Cell., 6(1): 42-54 (2015).
Zhang, Y. et al., Discovery of a Tetrahydroisoquinoline-Based Hydroxamic Acid Derivative (ZYJ-34c) as Histone Deacetylase Inhibitor with Potent Oral Antitumor Activities, J. Med. Chem., 54:5532-5539 (2011).
Zhang, Y. et al., Two Catalytic Domains Are Required for Protein Deacetylation, The Journal of Biological Chemistry, 281(5):2401-2404 (2006).

BICYCLIC [4,6,0] HYDROXAMIC ACIDS AS HDAC INHIBITORS

CROSS-REFERENCE TO RELATED APPLICATIONS

This application is a divisional of Ser. No. 16/522,082, filed Jul. 25, 2019, which is a divisional of U.S. application Ser. No. 16/199,489, filed Nov. 26, 2018, which is a divisional of U.S. application Ser. No. 15/013,811, filed Feb. 2, 2016, which claims the benefit of priority of U.S. Provisional Application No. 62/110,719, filed Feb. 2, 2015, the contents of each of which are hereby incorporated by reference.

FIELD OF THE INVENTION

The present invention relates to inhibitors of zinc-dependent histone deacetylases (HDACs) useful in the treatment of diseases or disorders associated with HDACs including cell proliferation diseases (e.g., cancer), neurological and inflammatory diseases. Specifically, this invention is concerned with compounds and compositions inhibiting HDACs, methods of treating diseases associated with HDACs, and methods of synthesizing these compounds.

BACKGROUND OF THE INVENTION

Many members of the HDAC family require zinc (Zn) to function properly. For instance, the isozyme histone deacetylase 6 (HDAC6) is a zinc-dependent histone deacetylase that possesses histone deacetylase activity. Other family members include HDACs 1-5 and 7-11. (De Ruijter et al, Biochem. J. 2003. 370; 737-749).

HDAC6 is known to deacetylate and associate with α-tubulin, cortactin, heat shock protein 90, ß-catenin, glucose-regulated protein 78 kDa, myosin heavy chain 9, heat shock cognate protein 70, and dnaJ homolog subfamily A member 1 (reviewed in Li et al, FEBS J. 2013, 280: 775-93; Zhang et al, Protein Cell. 2015, 6(1): 42-54). Diseases in which HDAC6 inhibition could have a potential benefit include cancer (reviewed in Aldana-Masangkay et al, J. Biomed. Biotechnol. 2011, 875824), specifically: multiple myeloma (Hideshima et al, Proc. Natl. Acad. Sci USA 2005, 102(24):8567-8572); lung cancer (Kamemura et al, Biochem. Biophys. Res. Commun. 2008, 374(1):84-89); ovarian cancer (Bazzaro et al, Clin. Cancer Res. 2008, 14(22):7340-7347); breast cancer (Lee et al, Cancer Res. 2008, 68(18):7561-7569; Park et al, Oncol. Rep. 2011, 25: 1677-81; Rey et al, Eur. J. Cell Biol. 2011, 90: 128-35); prostate cancer (Seidel et al, Biochem Pharmacol. 2015 (15)00714-5); pancreatic cancer (Nawrocki et al, Cancer Res. 2006, 66(7):3773-3781); renal cancer (Cha et al, Clin. Cancer Res. 2009, 15(3): 840-850); hepatocellular cancer (Ding et al, FEBS Lett. 2013, 587:880-6; Kanno et al, Oncol. Rep. 2012, 28: 867-73); lymphomas (Ding et al, Cancer Cell Int. 2014, 14:139; Amengual et al, Clin Cancer Res. 2015, 21(20):4663-75); and leukemias such as acute myeloid leukemia (AML) (Fiskus et al, Blood 2008, 112(7):2896-2905) and acute lymphoblastic leukemia (ALL) (Rodriguez-Gonzalez et al, Blood 2008, 1 12(11): Abstract 1923)).

Inhibition of HDAC6 may also have a role in cardiovascular disease, including pressure overload, chronic ischemia, and infarction-reperfusion injury (Tannous et al, Circulation 2008, 1 17(24):3070-3078); bacterial infection, including those caused by uropathogenic Escherichia coli (Dhakal and Mulve, J. Biol. Chem. 2008, 284(1):446-454); neurological diseases caused by accumulation of intracellular protein aggregates such as Alzheimer's, Parkinson's and Huntington's disease (reviewed in Simoes-Pires et al, Mol Neurodegener. 2013, 8: 7) or central nervous system trauma caused by tissue injury, oxidative-stress induced neuronal or axomal degeneration (Rivieccio et al, Proc. Natl. Acad. Sci. USA 2009, 106(46):19599-195604); and inflammation and autoimmune diseases through enhanced T cell-mediated immune tolerance at least in part through effects on regulatory T cells, including rheumatoid arthritis, psoriasis, spondylitis arthritis, psoriatic arthritis, multiple sclerosis, lupus, colitis and graft versus host disease (reviewed in Wang et al, Nat. Rev. Drug Disc. 2009 8(12):969-981; Vishwakarma et al, Int Immunopharmacol. 2013, 16:72-8; Kalin et al, J. Med Chem. 2012, 55:639-51); and fibrotic disease, including kidney fibrosis (Choi et al, Vascul Pharmacol. 2015 72:130-140).

Four HDAC inhibitors are currently approved for the treatment of some cancers. These are suberanilohydroxamic acid (Vorinostat; Zolinza®) for the treatment of cutaneous T cell lymphoma and multiple myeloma; Romidepsin (FK228; FR901228; Istodax®) for the treatment of peripheral T cell lymphoma; Panobinostat (LBH-589; Farydak®) for the treatment of multiple myeloma; and belinostat (PXD101; Beleodaq®) for the treatment of peripheral T cell lymphoma. However, these drugs are of limited effectiveness and can give rise to unwanted side effects. Thus there is a need for drugs with an improved safety-efficacy profile.

Given the complex function of HDAC6 and their potential utility in the treatment of proliferative diseases, neurological diseases, and inflammatory diseases, there is a need for HDAC inhibitors (e.g., HDAC6 inhibitors) with good therapeutic properties.

SUMMARY OF THE INVENTION

One aspect of the invention relates to compounds of Formula I:

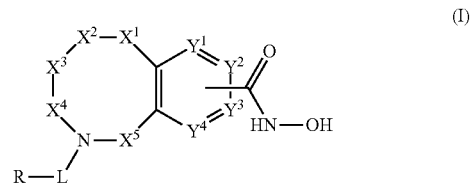

and pharmaceutically acceptable salts, prodrugs, solvates, hydrates, tautomers and isomers thereof, wherein:

$X^1$ and $X^2$ are each independently $CR^1R^2$, $NR^3$, O, C=O, $SO_2$, S(O) or S;

$X^3$, $X^4$ and $X^5$ are each independently $CR^1R^2$, C=O, S(O) or $SO_2$;

$Y^1$ and $Y^4$ are each independently N or $CR^1$;

$Y^2$ and $Y^3$ are each independently N or $CR^1$ when not bonded to —C(O)NHOH and $Y^2$ and $Y^3$ are C when bonded to —C(O)NHOH;

L is a bond, —$(CR^1R^2)$—, —C(O)—, —C(O)O—, —C(O)$NR^3$—, —S(O)$_2$—, —S(O)$_2NR^3$—, —S(O)—, —S(O)$NR^3$—, —C(O)$(CR^1R^2)_n$O—, or —C(O)$(CR^1R^2)_n$—;

R is independently, and at each occurrence, —H, —$C_1$-$C_6$alkyl, —$C_2$-$C_6$alkenyl, $C_8$cycloalkenyl, —$C_2$-$C_6$alkynyl, —$C_3$-$C_8$cycloalkyl, —$C_5$-$C_{12}$spirocycle, heterocyclyl, spiroheterocyclyl, aryl, or heteroaryl containing 1-5 heteroatoms selected from the group consisting of N, S, P, or O, wherein each alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —NO$_2$, —CN, —R$^2$, —OR$^3$, —NHR$^3$, —NR$^3$R$^4$, —S(O)$_2$NR$^3$R$^4$, —S(O)$_2$R$^1$, —C(O)R$^1$, —CO$_2$R$^1$, —NR$^3$S(O)$_2$R$^1$, —S(O)R$^1$, —S(O)NR$^3$R$^4$, —NR$^3$S(O)R$^1$, heterocycle, aryl, or heteroaryl, with the proviso that when L is —C(O)— the spiroheterocyclyl is not bound to L via a nitrogen atom;

R$^1$ and R$^2$ are independently, and at each occurrence, —H, R$^3$, R$^4$, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P, or O, —OH, halogen, —NO$_2$, —CN, —NHC$_1$-C$_6$alkyl, —N(C$_1$-C$_6$alkyl)$_2$, —S(O)$_2$N(C$_1$-C$_6$alkyl)$_2$, —N(C$_1$-C$_6$alkyl)S(O)$_2$R$^5$, —S(O)$_2$(C$_1$-C$_6$alkyl), —(C$_1$-C$_6$alkyl)S(O)$_2$R$^5$, —C(O)C$_1$-C$_6$alkyl, —CO$_2$C$_1$-C$_6$alkyl, —N(C$_1$-C$_6$alkyl)S(O)$_2$C$_1$-C$_6$alkyl, or (CHR$^5$)$_n$NR$^3$R$^4$, wherein each alkyl, alkenyl, cycloalkenyl, alkynyl, cycloalkyl, heterocyclyl, aryl, or heteroaryl is optionally substituted with one or more substituents selected from —OH, halogen, —NO$_2$, oxo, —CN, —R$^5$, —OR$^3$, —NHR$^3$, NR$^3$R$^4$, —S(O)$_2$N(R$^3$)$_2$—, —S(O)$_2$R$^5$, —C(O)R$^5$, —CO$_2$R$^5$, —NR$^3$S(O)$_2$R$^5$, —S(O)R$^5$, —S(O)NR$^3$R$^4$, —NR$^3$S(O)R$^5$, heterocycle, aryl, or heteroaryl containing 1-5 heteroatoms selected from the group consisting of N, S, P, or O;

or R$^1$ and R$^2$ may combine with the carbon atom to which they are both attached to form a spirocycle, spiroheterocycle, or a spirocycloalkenyl;

or R$^1$ and R$^2$, when on adjacent atoms, can combine to form a heterocycle, cycloalkyl, aryl, heteroaryl containing 1-5 heteroatoms selected from the group consisting of N, S, P, or O, or cycloalkenyl;

or R$^1$ and R$^2$, when on non-adjacent atoms, can combine to form a bridging cycloalkyl or heterocycloalkyl wherein the bridge between X$^1$ and X$^4$ cannot contain exactly one carbon;

R$^3$ and R$^4$ are independently, and at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P, or O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —CO$_2$C$_1$-C$_6$alkyl, or —(CHR$^5$)$_n$N(C$_1$-C$_6$alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O(C$_1$-C$_6$)alkyl, —NH(C$_1$-C$_6$)alkyl, N(C$_1$-C$_6$alkly)$_2$, —S(O)$_2$N(C$_1$-C$_6$alkyl)$_2$, —S(O)$_2$NHC$_1$-C$_6$alkyl, —C(O)C$_1$-C$_6$alkyl, —CO$_2$C$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocycle, aryl, or heteroaryl containing 1-5 heteroatoms selected from the group consisting of N, S, P, or O;

R$^5$ is independently, and at each occurrence, —H, —C$_1$-C$_6$alkyl, —C$_2$-C$_6$alkenyl, —C$_3$-C$_8$cycloalkenyl, —C$_2$-C$_6$alkynyl, —C$_3$-C$_8$cycloalkyl, heterocyclyl, aryl, heteroaryl, —OH, halogen, —NO$_2$, —CN, —NHC$_1$-C$_6$alkyl, —N(C$_1$-C$_6$alkyl)$_2$, —S(O)$_2$NH(C$_1$-C$_6$alkyl), —S(O)$_2$N(C$_1$-C$_6$alkyl)$_2$, —S(O)$_2$C$_1$-C$_6$alkyl, —C(O)C$_1$-C$_6$alkyl, —CO$_2$C$_1$-C$_6$alkyl, —N(C$_1$-C$_6$alkyl)SO$_2$C$_1$-C$_6$alkyl, —S(O)(C$_1$-C$_6$alkyl), —S(O)N(C$_1$-C$_6$alkyl)$_2$, —N(C$_1$-C$_6$alkyl)S(O)(C$_1$-C$_6$alkyl) or (CH$_2$)$_n$N(C$_1$-C$_6$alkyl)$_2$; and n is independently, and at each occurrence, an integer from 0 to 6;

provided that X$^1$, X$^2$, X$^3$, X$^4$ and X$^5$ are not all CR$^1$R$^2$ at the same time.

Another aspect of the invention relates to compounds of Formula II:

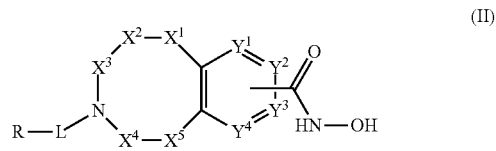

(II)

and pharmaceutically acceptable salts, prodrugs, solvates, hydrates, tautomers and isomers thereof, wherein:

X$^1$ is independently CR$^1$R$^2$, NR$^3$, O, C=O, SO$_2$, S(O) or S;

X$^2$, X$^3$, X$^4$ and X$^5$ are each independently CR$^1$R$^2$, C=O, S(O) or SO$_2$;

Y$^1$ and Y$^4$ are each independently N or CR$^1$;

Y$^2$ and Y$^3$ are each independently N or CR$^1$ when not bonded to —C(O)NHOH and Y$^2$ and Y$^3$ are C when bonded to —C(O)NHOH;

L is a bond, —(CR$^1$R$^2$)$_n$—, —C(O)—, —C(O)O—, —C(O)NR$^3$—, —S(O)$_2$—, —S(O)$_2$NR$^3$—, —S(O)—, —S(O)NR$^3$—, —C(O)(CR$^1$R$^2$)$_n$O—, or —C(O)(CR$^1$R$^2$)$_n$—;

R is independently, and at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —C$_5$-C$_{12}$spirocycle, heterocyclyl, spiroheterocyclyl, aryl, or heteroaryl containing 1-5 heteroatoms selected from the group consisting of N, S, P, or O, wherein each alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —NO$_2$, —CN, —R$^2$, —OR$^3$, —NHR$^3$, —NR$^3$R$^4$, —S(O)$_2$NR$^3$R$^4$, —S(O)$_2$R$^1$, —C(O)R$^1$, or —CO$_2$R$^1$, —NR$^3$S(O)$_2$R$^1$, —S(O)R$^1$, —S(O)NR$^3$R$^4$, —NR$^3$S(O)R$^1$, heterocycle, aryl, or heteroaryl, with the proviso that when L is —C(O)— the spiroheterocyclyl is not bound to L via a nitrogen atom;

R$^1$ and R$^2$ are independently, and at each occurrence, —H, R$^3$, R$^4$, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P, or O, —OH, halogen, —NO$_2$, —CN, —NHC$_1$-C$_6$alkyl, —N(C$_1$-C$_6$alkyl)$_2$, —S(O)$_2$N(C$_1$-C$_6$alkyl)$_2$, —N(C$_1$-C$_6$alkyl)S(O)$_2$R$^5$, —S(O)$_2$(C$_1$-C$_6$alkyl), —(C$_1$-C$_6$alkyl)S(O)$_2$R$^5$, —C(O)C$_1$-C$_6$alkyl, —CO$_2$C$_1$-C$_6$alkyl, —N(C$_1$-C$_6$alkyl)S(O)$_2$C$_1$-C$_6$alkyl, or (CHR$^5$)$_n$NR$^3$R$^4$, wherein each alkyl, alkenyl, cycloalkenyl, alkynyl, cycloalkyl, heterocyclyl, aryl, or heteroaryl is optionally substituted with one or more substituents selected from —OH, halogen, —NO$_2$, oxo, —CN, —R$^5$, —OR$^3$, —NHR$^3$, NR$^3$R$^4$, —S(O)$_2$N(R$^3$)$_2$—, —S(O)$_2$R$^5$, —C(O)R$^5$, —CO$_2$R$^5$, —NR$^3$S(O)$_2$R$^5$, —S(O)R$^5$, —S(O)NR$^3$R$^4$, —NR$^3$S(O)R$^5$, heterocycle, aryl, or heteroaryl;

or R$^1$ and R$^2$ may combine with the carbon atom to which they are both attached to form a spirocycle, spiroheterocycle, or a spirocycloalkenyl;

or R$^1$ and R$^2$, when on adjacent atoms, can combine to form a heterocycle, cycloalkyl, aryl, heteroaryl containing 1-5 heteroatoms selected from the group consisting of N, S, P, or O, or cycloalkenyl;

or R$^1$ and R$^2$, when on non-adjacent atoms, can combine to form a bridging cycloalkyl or heterocycloalkyl;

$R^3$ and $R^4$ are independently, and at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P, or O, —S(O)$_2$N($C_1$-$C_6$alkyl)$_2$, —S(O)$_2$($C_1$-$C_6$alkyl), —($C_1$-$C_6$alkyl)S(O)$_2$R$^5$, —C(O)$C_1$-$C_6$alkyl, —CO$_2$$C_1$-$C_6$alkyl, or —(CHR$^5$)$_n$N($C_1$-$C_6$alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O($C_1$-$C_6$)alkyl, —NH($C_1$-$C_6$)alkyl, N($C_1$-$C_6$alkly)$_2$, —S(O)$_2$N($C_1$-$C_6$alkyl)$_2$, —S(O)$_2$NH$C_1$-$C_6$alkyl, —C(O)$C_1$-$C_6$alkyl, —CO$_2$$C_1$-$C_6$alkyl, —N($C_1$-$C_6$alkyl)S(O)$_2$$C_1$-$C_6$alkyl, —S(O)R$^5$, —S(O)N($C_1$-$C_6$alkyl)$_2$, —N($C_1$-$C_6$alkyl)S(O)R$^5$, heterocycle, aryl, or heteroaryl containing 1-5 heteroatoms selected from the group consisting of N, S, P, or O;

$R^5$ is independently, and at each occurrence, —H, —$C_1$-$C_6$alkyl, —$C_2$-$C_6$alkenyl, —$C_3$-$C_8$cycloalkenyl, —$C_2$-$C_6$alkynyl, —$C_3$-$C_8$cycloalkyl, heterocyclyl, aryl, heteroaryl, —OH, halogen, —NO$_2$, —CN, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2$$C_1$-$C_6$alkyl, —C(O)$C_1$-$C_6$alkyl, —CO$_2$$C_1$-$C_6$alkyl, —N($C_1$-$C_6$alkyl)SO$_2$$C_1$-$C_6$alkyl, —S(O)($C_1$-$C_6$alkyl), —S(O)N($C_1$-$C_6$alkyl)$_2$, —N($C_1$-$C_6$alkyl)S(O)($C_1$-$C_6$alkyl) or (CH$_2$)$_n$N($C_1$-$C_6$alkyl)$_2$; and n is independently and at each occurrence an integer from 0 to 6;

provided that $X^1$, $X^2$, $X^3$, $X^4$ and $X^5$ are not all CR$^1$R$^2$ at the same time.

Another aspect of the invention relates to a method of treating a disease or disorder associated with HDAC6 modulation in a subject in need thereof, comprising administering to the subject an effective amount of a compound of Formulae I or II.

Another aspect of the invention is directed to a method of inhibiting HDAC6. The method involves administering to a patient in need thereof an effective amount of a compound of Formulae I or II.

Another aspect of the invention is directed to pharmaceutical compositions comprising a compound of Formulae I or II and a pharmaceutically acceptable carrier. The pharmaceutically acceptable carrier can further include an excipient, diluent, or surfactant. The pharmaceutical composition can be effective for treating a disease or disorder associated with HDAC6 modulation in a subject in need thereof. The pharmaceutical compositions can comprise the compounds of the present invention for use in treating diseases described herein. The compositions can contain at least one compound of the invention and a pharmaceutically acceptable carrier. The invention also provides the use of the compounds described herein in the manufacture of a medicament for the treatment of a disease associated with HDACs.

The present invention also provides methods for the treatment of human diseases or disorders including, without limitation, oncological, neurological, inflammatory, autoimmune, infectious, metabolic, hematologic, or cardiovascular diseases or disorders.

The present invention also provides compounds that are useful in inhibiting of zinc-dependent HDAC enzymes, and in particular HDAC6. These compounds can also be useful in the treatment of diseases including cancer.

The present invention further provides compounds that can inhibit HDAC6. In some embodiments, the efficacy-safety profile of the compounds of the current invention can be improved relative to other known HDAC (e.g. HDAC6) inhibitors. Additionally, the present technology also has the advantage of being able to be used for a number of different types of diseases, including cancer and non-cancer indications. Additional features and advantages of the present technology will be apparent to one of skill in the art upon reading the Detailed Description of the Invention, below.

DETAILED DESCRIPTION OF THE INVENTION

HDAC6 is a zinc-dependent histone deacetylase that has two catalytic domains. HDAC6 can interact with and deacetylate non-histone proteins, including HSP90 and α-tubulin. Acetylation of HSP90 is associated with loss of function of HSP90. HDAC6 is also implicated in the degradation of misfolded proteins as part of the aggresome. Accordingly, inhibition of HDAC6 can have downstream effects that can play a role in the development of certain diseases such as cancer. The present invention provides inhibitors of HDAC6 and methods for using the same to treat disease.

In a first aspect of the invention, compounds of the Formulae I or II are described:

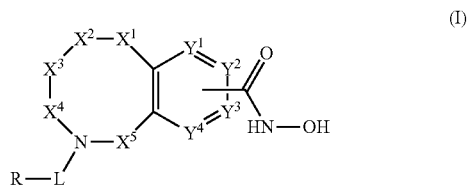

and pharmaceutically acceptable salts, prodrugs, solvates, hydrates, tautomers, and isomers thereof, wherein R, L, $X^1$, $X^2$, $X^3$, $X^4$, $X^5$, $Y^1$, $Y^2$, $Y^3$, and $Y^4$ are described as above.

In a second aspect of the invention, compounds of the Formula II are described:

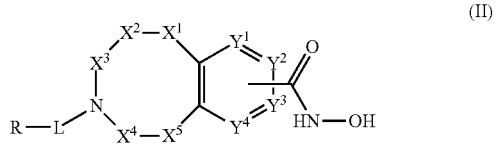

and pharmaceutically acceptable salts, prodrugs, solvates, hydrates, tautomers, and isomers thereof, wherein R, L, $X^1$, $X^2$, $X^3$, $X^4$, $X^5$, $Y^1$, $Y^2$, $Y^3$, and $Y^4$ are described as above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, halogen, —O—$C_1$-$C_6$alkyl, —$C_1$-$C_6$alkyl, —$OC_2$-$C_6$alkenyl, —$OC_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —NH$_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 24 ring atoms or a polycyclic aromatic radical, containing one or more ring heteroatoms selected from N, S, P, or O, the remaining ring atoms being C. Heteroaryl as herein defined also means a bicyclic heteroaromatic group wherein the heteroatom is selected from N, S, P, or O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

"Alkyl" refers to a straight or branched chain saturated hydrocarbon. $C_1$-$C_6$alkyl groups contain 1 to 6 carbon atoms. Examples of a $C_1$-$C_6$alkyl group include, but are not limited to, methyl, ethyl, propyl, butyl, pentyl, isopropyl, isobutyl, sec-butyl and tert-butyl, isopentyl and neopentyl.

The term "alkenyl" means an aliphatic hydrocarbon group containing a carbon carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkynyl" means an aliphatic hydrocarbon group containing a carbon carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 3-18 carbon atoms. Examples of cycloalkenyl groups include, without limitation, cyclopentenyl, cyclohexenyl, cycloheptenyl, cyclooctenyl, and norborenyl. A $C_3$-$C_8$ cycloalkenyl is a cycloalkenyl group containing between 3 and 8 carbon atoms.

The terms "heterocyclyl" or "heterocycloalkyl" or "heterocycle" refer to monocyclic or polycyclic 3 to 24-membered rings containing carbon and heteroatoms taken from oxygen, nitrogen, or sulfur and wherein there is not delocalized π electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocycloalkyl ring can also be fused or bridged, e.g., can be a bicyclic ring.

As used herein, the term "halo" or "halogen" means fluoro, chloro, bromo, or iodo.

The term "carbonyl" refers to a functional group composing a carbon atom double-bonded to an oxygen atom. It can be abbreviated herein as "oxo", as C(O), or as C=O.

"Spirocycle" or "spirocyclic" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A $C_3$-$C_{12}$ spirocycle is a spirocycle containing between 3 and 12 carbon atoms. One or more of the carbon atoms can be substituted with a heteroatom.

The term "spirocyclic heterocycle" or "spiroheterocycle" is understood to mean a spirocycle wherein at least one of the rings is a heterocycle (e.g., at least one of the rings is furanyl, morpholinyl, or piperadinyl).

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "stereoisomers" refers to the set of compounds which have the same number and type of atoms and share the same bond connectivity between those atoms, but differ in three dimensional structure. The term "stereoisomer" refers to any member of this set of compounds.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. In some cases these diastereomers were separated and in other cases a wavy bond is used to indicate the structural element where configuration is variable.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the invention.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formulae I or II may have one or more asymmetric carbon atom and may occur as racemates, racemic mixtures and as individual enantiomers or diastereomers.

A "patient" or "subject" is a mammal, e.g., a human, mouse, rat, guinea pig, dog, cat, horse, cow, pig, or non-human primate, such as a monkey, chimpanzee, baboon or rhesus.

In one embodiment of the compounds of Formula I, $X^5$ is $CR^1R^2$.

In another embodiment of the compounds of Formula I, $X^1$ is $NR^3$, O, C=O, $SO_2$, or S.

In another embodiment of the compounds of Formula I, $X^1$ is O and $X^5$ is $CR^1R^2$.

In another embodiment of the compounds of Formula I, L is $CH_2$.

In another embodiment of the compounds of Formula I, L is —C(O)—.

In another embodiment of the compounds of Formula I, any two or more of $R^1$ and $R^2$ may combine with the carbon atom or atoms to which they are attached to form a heterocycle, a cycloalkyl, or a spirocycle only when $X^1$ is O, S, or N.

In another embodiment of the compounds of Formula I, any two or more of $R_1$ and $R^2$ when on adjacent atoms, may attach to form a heterocycle, cycloalkyl, aryl, heteroaryl containing 1-5 heteroatoms, or cycloalkenyl only when $X^1$ is O, S, or N.

In another embodiment of the compounds of Formula I, any two or more of $R^1$, and $R^2$, when on non-adjacent atoms, can combine to form a bridging cycloalkyl or heterocycloalkyl only when $X^1$ is O, S, or N.

In one embodiment of the compounds of Formula II, $X^5$ is $CR^1R^2$.

In another embodiment of the compounds of Formula II, $X^1$ is $NR^3$, O, C=O, $SO_2$, or S.

In another embodiment of the compounds of Formula II, $X^1$ is O and $X^5$ is $CR^1R^2$.

In another embodiment of the compounds of Formula II, L is $CH_2$.

In another embodiment of the compounds of Formula II, L is —C(O)—.

In another embodiment of the compounds of Formula II, any two or more of $R^1$, and $R^2$ may combine with the carbon atom or atoms to which they are attached to form a heterocycle, a cycloalkyl, or a spirocycle only when $X^1$ is O, S, or N; or two or more of $R^1$ and $R^2$ when on adjacent atoms, may attach to form a heterocycle, cycloalkyl, aryl, heteroaryl containing 1-5 heteroatoms, or cycloalkenyl only when $X^1$ is O, S, or N; or two or more of $R^1$ and $R^2$, when on non-adjacent atoms, can combine to form a bridging cycloalkyl or heterocycloalkyl only when $X^1$ is O, S, or N.

In one embodiment, when $X^2$ and $X^5$ are both C=O, $X^1$ is not $NR^5$.

In one embodiment of the compounds of Formula I are described compounds of the Formula IA:

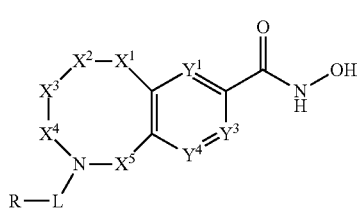

(IA)

and pharmaceutically acceptable salts, prodrugs, solvates, hydrates, tautomers or isomer thereof; where R, L, $X^1$, $X^2$, $X^3$, $X^4$, $X^5$, $Y^1$, $Y^3$, and $Y^4$ are defined as above in Formula I.

In some embodiments of the invention, the compounds of Formula IA may be of the formula IA-1:

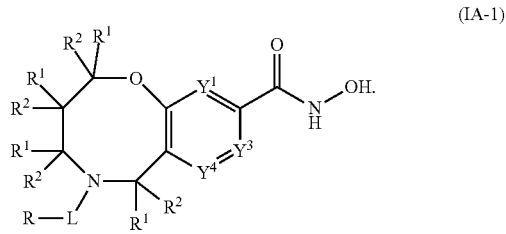

(IA-1)

In other embodiments of the compounds of Formula IA, the compound is of the formula IA-2:

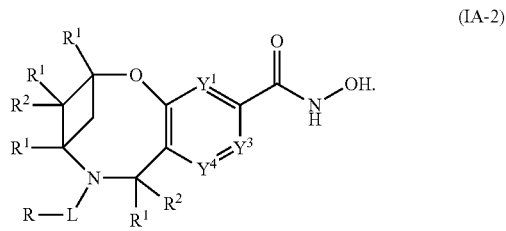

(IA-2)

In yet other another embodiments of the compounds of Formula IA, the compound is of the formula IA-3:

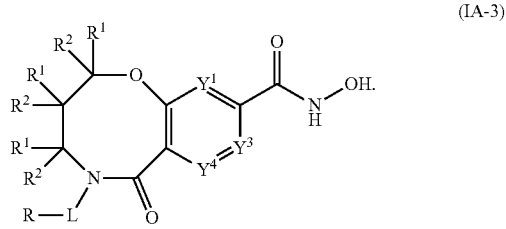

(IA-3)

In one embodiment of the compounds of Formula I are also disclosed compounds of the Formula IB:

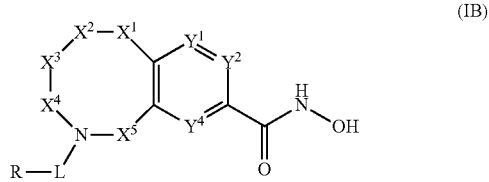

(IB)

and pharmaceutically acceptable salts, prodrugs, solvates, hydrates, enantiomers and isomers thereof where R, L, $X^1$, $X^2$, $X^3$, $X^4$, $X^5$, $Y^1$, $Y^2$, and $Y^4$ are defined as above in Formula I.

In one embodiment of the compounds of Formula II are described compounds of the Formula IIA:

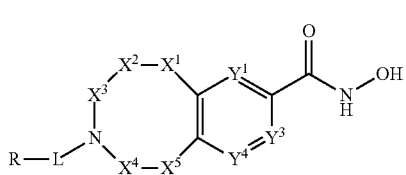

(IIA)

and pharmaceutically acceptable salts, prodrugs, solvates, hydrates, tautomers or isomer thereof; where R, L, $X^1$, $X^2$, $X^3$, $X^4$, $X^5$, $Y^1$, $Y^3$, and $Y^4$ are defined as above in Formula II.

In other embodiments of the compounds of Formula IIA, the compound is of the formula IIA-1:

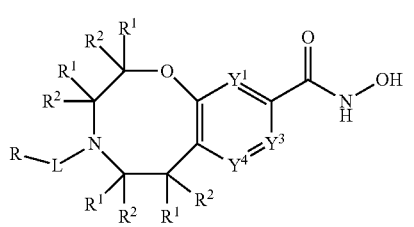

(IIA-1)

In yet other embodiments of the compounds of Formula IIA, the compound is of the formula (IIA-2):

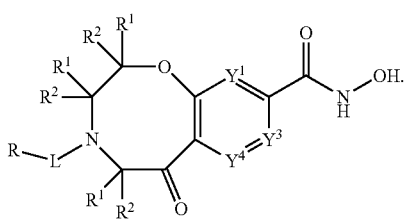

(IIA-2)

In other embodiments of the compounds of Formula II, the compound may also be of the formula II-B:

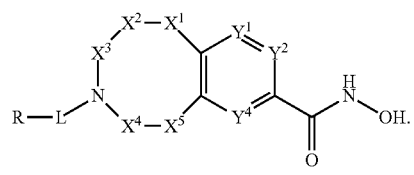

(II-B)

In some embodiments of Formula (I), $X^1$ is O. In another embodiment, $X^1$ is O and $X^2$ is $CR^1R^2$. In yet another embodiment, $X^1$ is O, $X^2$ is $CR^1R^2$, and $X^3$ is $CR^1R^2$. In another embodiment, $X^1$ is O, $X^2$ is $CR^1R^2$, $X^3$ is $CR^1R^2$, and $X^4$ is $CR^1R^2$. In yet another embodiment, $X^1$ is O, $X^2$ is $CR^1R^2$, $X^3$ is $CR^1R^2$, $X^4$ is $CR^1R^2$, and $X^5$ is $CR^1R^2$. In yet another embodiment, $X^1$ is O, $X^2$ is $CR^1R^2$, $X^3$ is $CR^1R^2$, $X^4$ is $CR^1R^2$, $X^5$ is $CR^1R^2$, and $Y^1$ is $CR^1$. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, and $Y^3$ is $CR^1$. In yet another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, and $Y^4$ is $CR^1$. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, and $Y^2$ is C. In yet another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —C(O)—. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is a bond. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —S(O)$_2$—. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —S(O)$_2$NR$^3$—. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —C(O)NR$^3$—. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —C(O)O—. In yet another embodiment, $X^1$ is O, $X^2$ is $CR^1R^2$, $X^3$ is $CR^1R^2$, $X^4$ is $CR^1R^2$, $Y^1$ is $CR^1$, $Y^3$ is $CR^1$, $Y^4$ is $CR^1$, $Y^2$ is C, L is —(CR$^1$R$^2$)n-.

In some embodiments of Formula (II), $X^1$ is O. In another embodiment, $X^1$ is O and $X^2$ is $CR^1R^2$. In yet another embodiment, $X^1$ is O, $X^2$ is $CR^1R^2$, and $X^3$ is $CR^1R^2$. In another embodiment, $X^1$ is O, $X^2$ is $CR^1R^2$, $X^3$ is $CR^1R^2$, and $X^4$ is $CR^1R^2$. In yet another embodiment, $X^1$ is O, $X^2$ is $CR^1R^2$, $X^3$ is $CR^1R^2$, $X^4$ is $CR^1R^2$, and $X^5$ is $CR^1R^2$. In yet another embodiment, $X^1$ is O, $X^2$ is $CR^1R^2$, $X^3$ is $CR^1R^2$, $X^4$ is $CR^1R^2$, $X^5$ is $CR^1R^2$, and $Y^1$ is $CR^1$. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, and $Y^3$ is $CR^1$. In yet another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, and $Y^4$ is $CR^1$. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, and $Y^2$ is C. In yet another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —C(O)—. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is a bond. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —S(O)$_2$—. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —S(O)$_2$NR$^3$—. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —C(O)NR$^3$—. In another embodiment, $X^1$ is O, $X^2$ is $CR^1R^2$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —C(O)O—. In yet another embodiment, $X^1$ is O, $X^2$ is $CR^1R^2$, $X^3$ is $CR^1R^2$, $X^4$ is $CR^1R^2$, $Y^1$ is $CR^1$, $Y^3$ is $CR^1$, $Y^4$ is $CR^1$, $Y^2$ is C, L is —(CR$^1$R$^2$)$_n$—.

In some embodiments of Formula (I), $X^2$ is NR$^3$. In another embodiment, $X^2$ is NR$^3$ and $X^1$ is $CR^1R^2$. In yet another embodiment, $X^1$ is $CR^1R^2$, $X^2$ is NR$^3$, and $X^3$ is $CR^1R^2$. In another embodiment, $X^1$ is $CR^1R^2$, $X^2$ is NR$^3$, $X^3$ is $CR^1R^2$, and $X^4$ is $CR^1R^2$. In yet another embodiment, $X^1$ is $CR^1R^2$, $X^2$ is NR$^3$, $X^3$ is $CR^1R^2$, $X^4$ is $CR^1R^2$, and $X^5$ is $CR^1R^2$. In yet another embodiment, $X^1$ is $CR^1R^2$, $X^2$ is NR$^3$, $X^3$ is $CR^1R^2$, $X^4$ is $CR^1R^2$, $X^5$ is $CR^1R^2$, and $Y^1$ is $CR^1$. In another embodiment, $X^1$ is $CR^1R^2$, $X^2$ is NR$^3$, $X^3$ is $CR^1R^2$, $X^4$ is $CR^1R^2$, $X^5$ is $CR^1R^2$, $Y^1$ is $CR^1$, and $Y^3$ is $CR^1$. In yet another embodiment, $X^1$ is $CR^1R^2$, $X^2$ is NR$^3$, $X^3$ is $CR^1R^2$, $X^4$ is $CR^1R^2$, $X^5$ is $CR^1R^2$, $Y^1$ is $CR^1$, $Y^3$ is $CR^1$, and $Y^4$ is $CR^1$. In another embodiment, $X^1$ is $CR^1R^2$, $X^2$ is $NR^3$, $X^3$ is $CR^1R^2$, $X^4$ is $CR^1R^2$, $X^5$ is $CR^1R^2$, $Y^1$ is $CR^1$, $Y^3$ is $CR^1R^2$, $Y^4$ is $CR^1$, and $Y^2$ is C. In yet another embodiment, $X^1$ is $CR^1R^2$, $X^2$ is $NR^3$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —C(O)—. In another embodiment, $X^1$ is $CR^1R^2$, $X^2$ is $NR^3$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is a bond. In another embodiment, $X^1$ is $CR^1R^2$, $X^2$ is $NR^3$, $X^3$ is $CR^1R^2$, $X^4$ is $CR^1R^2$, $X^5$ is $CR^1R^2$, Y is $CR^1$, $Y^3$ is $CR^1$, $Y^4$ is $CR^1$, $Y^2$ is C, and L is —S(O)$_2$—. In another embodiment $X^1$ is $CR^1R^2$, $X^2$ is $NR^3$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —S(O)$_2$NR$^3$—. In another embodiment, $X^1$ is $CR^1R^2$, $X^2$ is $NR^3$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —C(O)NR$^3$—. In another embodiment, $X^1$ is $CR^1R^2$, $X^2$ is $NR^3$, $X^3$ is $CR^1R^2$, $X^4$ is $CR^1R^2$, $X^5$ is $CR^1R^2$, $Y^1$ is $CR^1$, $Y^3$ is $CR^1$, $Y^4$ is $CR^1$, $Y^2$ is C, and L is —C(O)O—. In yet another embodiment, $X^1$ is $CR^1R^2$, $X^2$ is $NR^3$, $X^3$ is $CR^1R^2$, $X^4$ is $CR^1R^2$, $Y^1$ is $CR^1$, $Y^3$ is $CR^1$, $Y^4$ is $CR^1$, $Y^2$ is C, L is —(CR$^1$R$^2$)n-

In some embodiments of Formulae (I) and (II), R is H, —C$_1$-C$_6$ alkyl, —C$_4$-C$_8$ cycloalkenyl, —C$_3$-C$_8$ cycloalkyl, —C$_5$-C$_{12}$ spirocycle, heterocyclyl, spiroheterocyclyl, aryl, or heteroaryl containing 1 to 5 heteroatoms selected from the group consisting of N, S, P, and O, wherein each alkyl, cycloalkenyl, cycloalkyl, spirocycle, heterocyclyl, spiroheterocyclyl, aryl, or heteroaryl is optionally substituted with one or more —OH, halogen, oxo, —NO$_2$, —CN, —R$^2$, —OR$^3$, —NHR$^3$, —NR$^3$R$^4$, —S(O)$_2$NR$^3$R$^4$, —S(O)$_2$R$^1$, —C(O)R$^1$, or —CO$_2$R$^1$, —NR$^3$S(O)$_2$R$^1$, —S(O)R$^1$, —S(O)NR$^3$R$^4$, —NR$^3$S(O)R$^1$, heterocycle, aryl, or heteroaryl containing 1 to 5 heteroatoms selected from the group consisting of N, S, P, and O, with the proviso that R is not bound to L via a nitrogen atom.

In some embodiments of Formulae (I) and (II), n is 1 to 6. In another embodiment, n is 0 to 5. In yet another embodiment, n is 0 to 4. In yet another embodiment, n is 1 to 4. In another embodiment, n is 0 to 3. In yet another embodiment, n is 0 to 2. In yet another embodiment, n is 0 or 1. In another embodiment, n is 1 or 2.

In some embodiments of Formulae (I) and (II), $R^1$ and $R^2$ may combine with the atom to which they are both attached to form a spirocycle. In another embodiment, $R^1$ and $R^2$ combine with the atom to which they are both attached to form a spiroheterocycle. In another embodiment, $R^1$ and $R^2$ combine with the atom to which they are both attached to form a spirocycloalkenyl.

In some embodiments of Formulae (I) and (II), $R^1$ and $R^2$, when on adjacent atoms, combine to form a heterocycle. In another embodiment, $R^1$ and $R^2$, when on adjacent atoms, combine to form a cycloalkyl. In yet another embodiment, $R^1$ and $R^2$, when on adjacent atoms, combine to form a cycloalkenyl. In another embodiment, $R^1$ and $R^2$, when on adjacent atoms, combine to form an aryl. In yet another embodiment, $R^1$ and $R^2$, when on adjacent atoms, combine to form a heteroaryl containing 1 to 5 heteroatoms selected from the group consisting of N, S, P, and O.

In some embodiments of Formula (I), $R^1$ and $R^2$, when on non-adjacent atoms, combine to form a bridging cycloalkyl. In another embodiment, $R^1$ and $R^2$, when on non-adjacent atoms, combine to form a bridging cycloalkenyl. In yet another embodiment, $R^1$ and $R^2$, when on non-adjacent atoms, combine to form a heterocycloalkyl.

In an illustrative embodiment, the compound of Formula I is:

N-hydroxy-3,4,5,6-tetrahydro-2H-benzo[b][1,5]oxazocine-9-carboxamide;

N-hydroxy-5-(tetrahydro-2H-pyran-4-carbonyl)-3,4,5,6-tetrahydro-2H-benzo[b][1,5]oxazocine-9-carboxamide;

N-hydroxy-5-(4-methyltetrahydro-2H-pyran-4-carbonyl)-3,4,5,6-tetrahydro-2H-benzo[b][1,5]oxazocine-9-carboxamide;

N-hydroxy-5-phenyl-3,4,5,6-tetrahydro-2H-benzo[b][1,5]oxazocine-9-carboxamide;

5-benzyl-N-hydroxy-3,4,5,6-tetrahydro-2H-benzo[b][1,5]oxazocine-9-carboxamide;

5-benzoyl-N-hydroxy-3,4,5,6-tetrahydro-2H-benzo[b][1,5]oxazocine-9-carboxamide;

5-(cyclohexanecarbonyl)-N-hydroxy-3,4,5,6-tetrahydro-2H-benzo[b][1,5]oxazocine-9-carboxamide;

N-hydroxy-5-(phenylsulfonyl)-3,4,5,6-tetrahydro-2H-benzo[b][1,5]oxazocine-9-carboxamide;

N9-hydroxy-N5-phenyl-3,4-dihydro-2H-benzo[b][1,5]oxazocine-5,9(6H)-dicarboxamide;

N-hydroxy-5-(N-phenylsulfamoyl)-3,4,5,6-tetrahydro-2H-benzo[b][1,5]oxazocine-9-carboxamide;

5-(cyclohexylmethyl)-N-hydroxy-6-oxo-3,4,5,6-tetrahydro-2H-benzo[b][1,5]oxazocine-9-carboxamide;

N-hydroxy-5-phenyl-3,4,5,6-tetrahydro-2H-2,4-methanobenzo[b][1,5]oxazocine-9-carboxamide;

5-benzyl-N-hydroxy-3,4,5,6-tetrahydro-2H-2,4-methanobenzo[b][1,5]oxazocine-9-carboxamide;

5-benzoyl-N-hydroxy-3,4,5,6-tetrahydro-2H-2,4-methanobenzo[b][1,5]oxazocine-9-carboxamide;

5-(cyclohexanecarbonyl)-N-hydroxy-3,4,5,6-tetrahydro-2H-2,4-methanobenzo[b][1,5]oxazocine-9-carboxamide;

N-hydroxy-5-(tetrahydro-2H-pyran-4-carbonyl)-3,4,5,6-tetrahydro-2H-2,4-methanobenzo[b][1,5]oxazocine-9-carboxamide;

N-hydroxy-5-(phenylsulfonyl)-3,4,5,6-tetrahydro-2H-2,4-methanobenzo[b][1,5]oxazocine-9-carboxamide;

N9-hydroxy-N5-phenyl-3,4-dihydro-2H-2,4-methanobenzo[b][1,5]oxazocine-5,9(6H)-dicarboxamide;

N-hydroxy-5-(N-phenylsulfamoyl)-3,4,5,6-tetrahydro-2H-2,4-methanobenzo[b][1,5]oxazocine-9-carboxamide;

N-hydroxy-5-methyl-2-phenyl-1,2,3,4,5,6-hexahydrobenzo[f][1,4]diazocine-8-carboxamide;

2-benzyl-N-hydroxy-5-methyl-1,2,3,4,5,6-hexahydrobenzo[f][1,4]diazocine-8-carboxamide;

2-benzoyl-N-hydroxy-5-methyl-1,2,3,4,5,6-hexahydrobenzo[f][1,4]diazocine-8-carboxamide;

2-(cyclohexanecarbonyl)-N-hydroxy-5-methyl-1,2,3,4,5,6-hexahydrobenzo[f][1,4]diazocine-8-carboxamide;

N-hydroxy-5-methyl-2-(tetrahydro-2H-pyran-4-carbonyl)-1,2,3,4,5,6-hexahydrobenzo[f][1,4]diazocine-8-carboxamide;

N8-hydroxy-5-methyl-N2-phenyl-3,4,5,6-tetrahydrobenzo[f][1,4]diazocine-2,8(1H)-dicarboxamide;

N-hydroxy-5-methyl-2-(N-phenylsulfamoyl)-1,2,3,4,5,6-hexahydrobenzo[f][1,4]diazocine-8-carboxamide;

N-hydroxy-5-phenyl-3,4,5,6-tetrahydro-2H-benzo[b][1,5]oxazocine-8-carboxamide;

5-benzyl-N-hydroxy-3,4,5,6-tetrahydro-2H-benzo[b][1,5]oxazocine-8-carboxamide;

5-benzoyl-N-hydroxy-3,4,5,6-tetrahydro-2H-benzo[b][1,5]oxazocine-8-carboxamide;

5-(cyclohexanecarbonyl)-N-hydroxy-3,4,5,6-tetrahydro-2H-benzo[b][1,5]oxazocine-8-carboxamide;

N-hydroxy-5-(tetrahydro-2H-pyran-4-carbonyl)-3,4,5,6-tetrahydro-2H-benzo[b][1,5]oxazocine-8-carboxamide;

N-hydroxy-5-(phenylsulfonyl)-3,4,5,6-tetrahydro-2H-benzo[b][1,5]oxazocine-8-carboxamide;
N8-hydroxy-N5-phenyl-3,4-dihydro-2H-benzo[b][1,5]oxazocine-5,8(6H)-dicarboxamide;
N-hydroxy-5-(N-phenylsulfamoyl)-3,4,5,6-tetrahydro-2H-benzo[b][1,5]oxazocine-8-carboxamide;
5-(cyclohexylmethyl)-N-hydroxy-6-oxo-3,4,5,6-tetrahydro-2H-benzo[b][1,5]oxazocine-8-carboxamide;
N-hydroxy-5-phenyl-3,4,5,6-tetrahydro-2H-2,4-methanobenzo[b][1,5]oxazocine-8-carboxamide;
5-benzyl-N-hydroxy-3,4,5,6-tetrahydro-2H-2,4-methanobenzo[b][1,5]oxazocine-8-carboxamide;
5-benzoyl-N-hydroxy-3,4,5,6-tetrahydro-2H-2,4-methanobenzo[b][1,5]oxazocine-8-carboxamide;
5-(cyclohexanecarbonyl)-N-hydroxy-3,4,5,6-tetrahydro-2H-2,4-methanobenzo[b][1,5]oxazocine-8-carboxamide;
N-hydroxy-5-(tetrahydro-2H-pyran-4-carbonyl)-3,4,5,6-tetrahydro-2H-2,4-methanobenzo[b][1,5]oxazocine-8-carboxamide;
N-hydroxy-5-(phenylsulfonyl)-3,4,5,6-tetrahydro-2H-2,4-methanobenzo[b][1,5]oxazocine-8-carboxamide;
N8-hydroxy-N5-phenyl-3,4-dihydro-2H-2,4-methanobenzo[b][1,5]oxazocine-5,8(6H)-dicarboxamide;
N-hydroxy-5-(N-phenylsulfamoyl)-3,4,5,6-tetrahydro-2H-2,4-methanobenzo[b][1,5]oxazocine-8-carboxamide;
N-hydroxy-2-methyl-5-phenyl-1,2,3,4,5,6-hexahydrobenzo[f][1,4]diazocine-8-carboxamide;
5-benzyl-N-hydroxy-2-methyl-1,2,3,4,5,6-hexahydrobenzo[f][1,4]diazocine-8-carboxamide;
5-benzoyl-N-hydroxy-2-methyl-1,2,3,4,5,6-hexahydrobenzo[f][1,4]diazocine-8-carboxamide;
5-(cyclohexanecarbonyl)-N-hydroxy-2-methyl-1,2,3,4,5,6-hexahydrobenzo[f][1,4]diazocine-8-carboxamide;
N-hydroxy-2-methyl-5-(tetrahydro-2H-pyran-4-carbonyl)-1,2,3,4,5,6-hexahydrobenzo[f][1,4]diazocine-8-carboxamide;
N9-hydroxy-5-methyl-N2-phenyl-3,4,5,6-tetrahydrobenzo[f][1,4]diazocine-2,9(1H)-dicarboxamide; or
N-hydroxy-2-methyl-5-(N-phenylsulfamoyl)-1,2,3,4,5,6-hexahydrobenzo[f][1,4]diazocine-8-carboxamide.

In an illustrative embodiment the compound of Formula II is:
N-hydroxy-4-phenyl-3,4,5,6-tetrahydro-2H-benzo[g][1,4]oxazocine-9-carboxamide;
4-benzyl-N-hydroxy-3,4,5,6-tetrahydro-2H-benzo[g][1,4]oxazocine-9-carboxamide;
4-benzoyl-N-hydroxy-3,4,5,6-tetrahydro-2H-benzo[g][1,4]oxazocine-9-carboxamide;
4-(cyclohexanecarbonyl)-N-hydroxy-3,4,5,6-tetrahydro-2H-benzo[g][1,4]oxazocine-9-carboxamide;
N-hydroxy-4-(tetrahydro-2H-pyran-4-carbonyl)-3,4,5,6-tetrahydro-2H-benzo[g][1,4]oxazocine-9-carboxamide;
N-hydroxy-4-(phenylsulfonyl)-3,4,5,6-tetrahydro-2H-benzo[g][1,4]oxazocine-9-carboxamide;
N9-hydroxy-N4-phenyl-2,3,5,6-tetrahydro-4H-benzo[g][1,4]oxazocine-4,9-dicarboxamide;
4-(cyclohexylmethyl)-N-hydroxy-5-oxo-3,4,5,6-tetrahydro-2H-benzo[g][1,4]oxazocine-9-carboxamide;
N-hydroxy-4-phenyl-3,4,5,6-tetrahydro-2H-benzo[g][1,4]oxazocine-8-carboxamide;
4-benzyl-N-hydroxy-3,4,5,6-tetrahydro-2H-benzo[g][1,4]oxazocine-8-carboxamide;
4-benzoyl-N-hydroxy-3,4,5,6-tetrahydro-2H-benzo[g][1,4]oxazocine-8-carboxamide;
4-(cyclohexanecarbonyl)-N-hydroxy-3,4,5,6-tetrahydro-2H-benzo[g][1,4]oxazocine-8-carboxamide;
N-hydroxy-4-(tetrahydro-2H-pyran-4-carbonyl)-3,4,5,6-tetrahydro-2H-benzo[g][1,4]oxazocine-8-carboxamide;
N-hydroxy-4-(phenylsulfonyl)-3,4,5,6-tetrahydro-2H-benzo[g][1,4]oxazocine-8-carboxamide;
N8-hydroxy-N4-phenyl-2,3,5,6-tetrahydro-4H-benzo[g][1,4]oxazocine-4,8-dicarboxamide; or
4-(cyclohexylmethyl)-N-hydroxy-5-oxo-3,4,5,6-tetrahydro-2H-benzo[g][1,4]oxazocine-8-carboxamide.

In another embodiment, illustrative compounds of the invention include:
N-hydroxy-3,4,5,6-tetrahydro-2H-benzo[b][1,5]oxazocine-9-carboxamide;
N-hydroxy-5-(tetrahydro-2H-pyran-4-carbonyl)-3,4,5,6-tetrahydro-2H-benzo[b][1,5]oxazocine-9-carboxamide; and
N-hydroxy-5-(4-methyltetrahydro-2H-pyran-4-carbonyl)-3,4,5,6-tetrahydro-2H-benzo[b][1,5]oxazocine-9-carboxamide.

In another embodiment of the invention, the compounds of Formulae I or II are enantiomers. In some embodiments the compounds are the (S)-enantiomer. In other embodiments the compounds are the (R)-enantiomer. In yet other embodiments, the compounds of Formulae I or II may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Methods of Synthesizing the Disclosed Compounds

The compounds of the present invention may be made by a variety of methods, including standard chemistry. Suitable synthetic routes are depicted in the schemes given below.

The compounds of Formulae I or II may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formulae I or II.

Those skilled in the art will recognize if a stereocenter exists in the compounds of Formulae I or II. Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. These methods include but are not limited to those methods described below. Compounds of the present disclosure can be synthesized by following the steps outlined in General Schemes 1, 2, and 3 which comprise different sequences of assembling intermediates 2a, 2b, 2c, 2d, 2e, 2f, 2g, 2h, 2i, 2j, 2k, 2m, 2n, 2o, 2p, 2q, 2r, 2s, 2t, and 2u. Starting materials are either commercially available or made by known procedures in the reported literature or as illustrated.

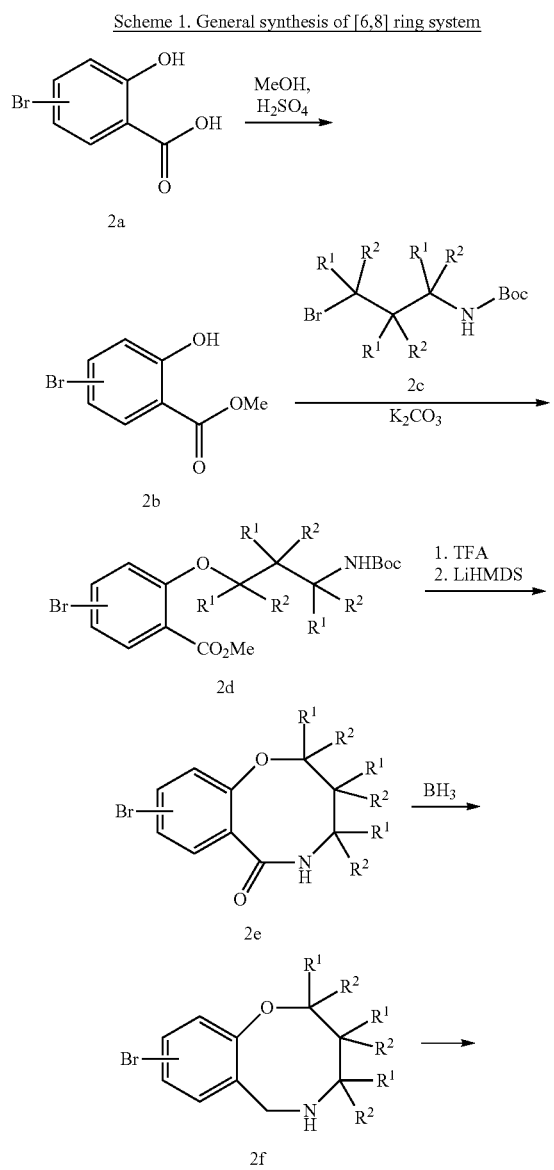

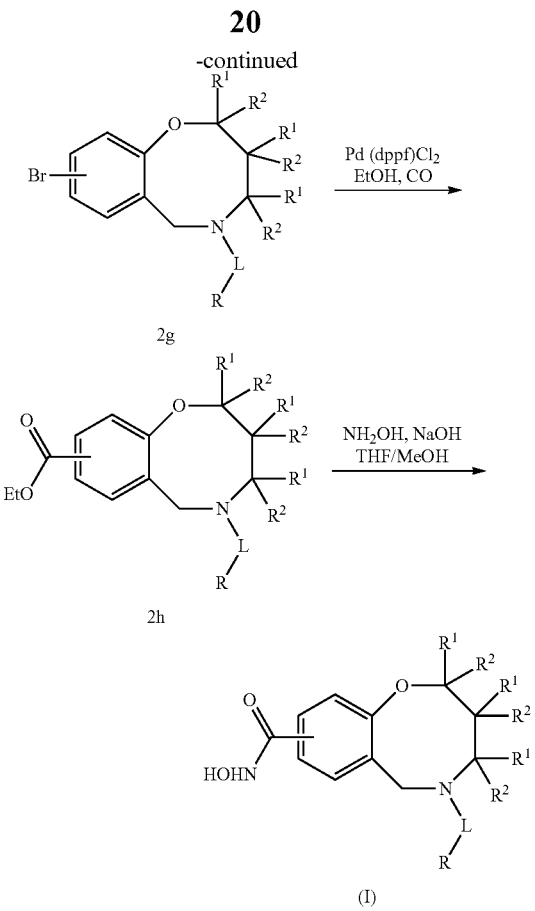

The general way of preparing target molecules of Formula (I) by using intermediates 2a, 2b, 2c, 2d, 2e, 2f, 2g, and 2h is outlined in General Scheme 1. Esterification of Intermediate 2a in an alcohol, e.g., methanol (MeOH) in the presence of an acid, e.g., sulfuric acid ($H_2SO_4$) provides Intermediate 2b. Nucleophilc addition of alcohol 2b to intermediate 2c using a base, e.g., potassium carbonate ($K_2CO_3$) in a solvent, e.g., acetone, provides Intermediate 2d. Deprotection of 2d with an acid, e.g., trifluoroacetic acid (TFA) in a solvent, e.g., dichloromethane, and subsequent cyclization in the presence of a base, e.g., LiHMDS provides intermediate 2e. Reduction of the amide linkage in 2e with a mild reducing agent, for instance, borane, in the presence of a solvent, e.g., tetrahydrofuran (THF) provides Intermediate 2f. Addition of the R-L moiety can be achieved via alkylation, reductive amination, arylation, acylation, sulfonation, or coupling reactions. For example, coupling of a carboxylic acid with Intermediate 2f under standard coupling conditions using a coupling reagent, e.g., 1-[bis(dimethyl amino)methylene]-1H-1,2,3-triazolo[4,5-b]pyridinium3-oxide hexafluoro-phosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., DMF, provides Intermediate 2g. The coupled product 2g can be carbonylated in the presence of a metal catalyst e.g., [1,1'-bis(diphenylphosphino)ferrocene]dichloro palladium(II) and carbon monoxide in a solvent, e.g., ethanol to provide Intermediate 2h. Treatment of intermediate 2h with hydroxylamine and a base, e.g., aqueous sodium hydroxide (NaOH (aq)) in a solvent, e.g., tetrahydrofuran and/or methanol provides compounds of Formula (I).

Scheme 2. General synthesis of bridged ring systems

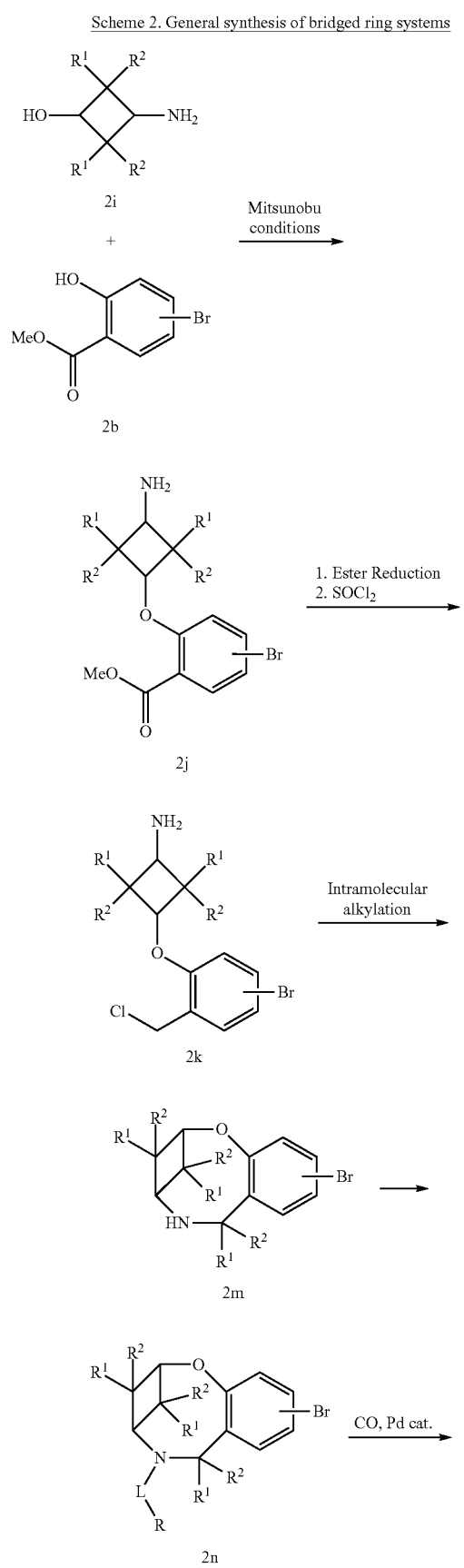

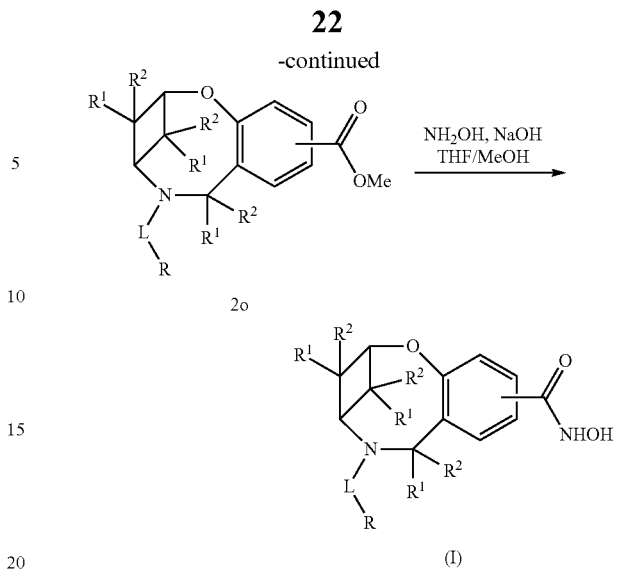

The general way of preparing target molecules of Formula (I) by using Intermediates 2b, 2i, 2j, 2k, 2m, 2n, and 2o is outlined in General Scheme 2. A secondary alcohol such as that of 2i is activated in the presence of, for instance, diethyl azodicarboxylate (DEAD) and triphenylphosphine (PPh$_3$) and in a solvent, e.g., tetrahydrofuran (THF) and reacted with the hydroxy group of Intermediate 2b to give Intermediate 2j. Reduction of the ester in 2j with a reducing agent, e.g., lithium aluminum hydride (LAH) in a solvent, e.g., tetrahydrofuran (THF) provides the corresponding alcohol which is converted to a primary benzyl chloride 2k by treating with thionyl chloride (SOCl$_2$) in a solvent, e.g., dichloromethane (DCM). An intramolecular nucleophilic substitution reaction in the presence of a base, e.g., potassium carbonate (K$_2$CO$_3$) in a solvent, e.g., dimethylformamide (DMF) provides intermediate 2m. Addition of the R-L moiety can be achieved via alkylation, reductive amination, arylation, acylation, sulfonation, or coupling reactions. For example, coupling of a carboxylic acid with Intermediate 2m under standard coupling conditions using a coupling reagent, e.g., 1-[bis(dimethyl amino)methylene]-1H-1,2,3-triazolo[4,5-b]pyridinium3-oxide hexafluoro-phosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., DMF, provides Intermediate 2n. The coupled product 2n can be carbonylated in the presence of a metal catalyst e.g., [1,1'-bis(diphenylphosphino)ferrocene]dichloro palladium(II) and carbon monoxide in a solvent, e.g., methanol to provide Intermediate 2o. Treatment of intermediate 2o with hydroxylamine and a base, e.g., aqueous sodium hydroxide (NaOH (aq)) in a solvent, e.g., tetrahydrofuran and/or methanol provides compounds of Formula (I).

Scheme 3. General synthesis of [6,8] systems of nucleophilc substitution

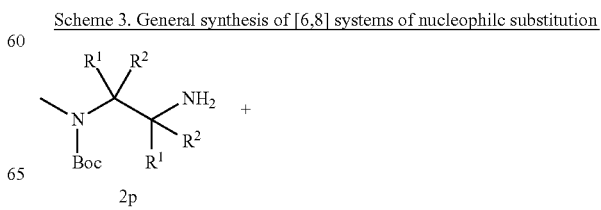

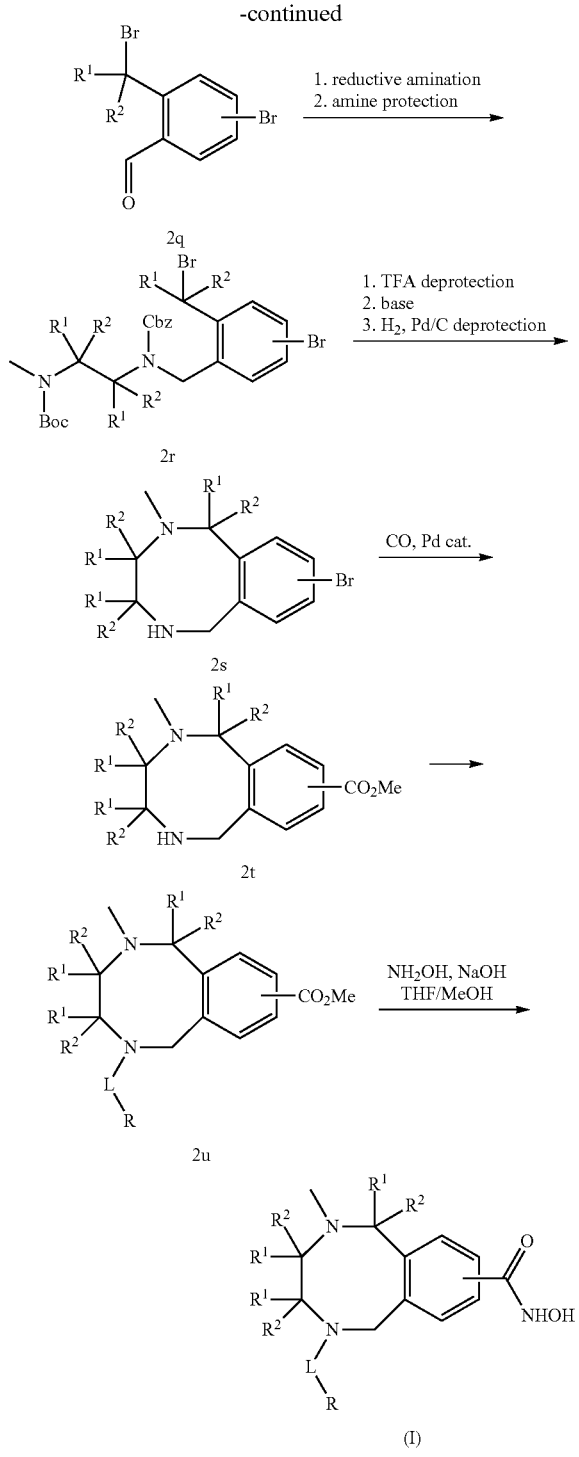

2r in the presence of an acid, e.g., trifluoroacetic acid (TFA), in a solvent, e.g., dichloromethane (DCM) followed by treatment with a base, e.g., potassium carbonate ($K_2CO_3$), completes an intramolecular nucleophilic substitution reaction to form a bicycle. Deprotection of the carboxybenzyl protecting group under an atmosphere of hydrogen with catalytic palladium on carbon affords Intermediate 2s. The deprotected product 2s can be carbonylated in the presence of a metal catalyst e.g., [1,1'-bis(diphenylphosphino)ferrocene]dichloro palladium(II)-dichloromethane adduct and carbon monoxide in a solvent, e.g., methanol to provide Intermediate 2t. Addition of the R-L moiety can be achieved via alkylation, reductive amination, arylation, acylation, sulfonation, or coupling reactions. For example, coupling of a carboxylic acid with Intermediate 2t under standard coupling conditions using a coupling reagent, e.g., 1-[bis(dimethylamino)methylene]-1H-1,2,3-triazolo[4,5-b]pyridinium3-oxide hexafluoro-phosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., DMF, provides Intermediate 2u. Treatment of intermediate 2u with hydroxylamine and a base, e.g., aqueous sodium hydroxide (NaOH (aq)) in a solvent, e.g., tetrahydrofuran and/or methanol provides compounds of Formula (I).

Methods of Using the Disclosed Compounds

Another aspect of the invention relates to a method of treating a disease associated with HDAC, e.g., HDAC6, modulation in a subject in need thereof. The method involves administering to a patient in need of treatment for diseases or disorders associated with HDAC, e.g., HDAC6, modulation an effective amount of a compound of Formula I. In an embodiment, the disease can be, but is not limited to, cancer, neurodegenerative disease, neurodevelopmental disease, inflammatory or autoimmune disease, infection, metabolic disease, hematologic disease, or cardiovascular disease.

Another aspect of the invention is directed to a method of inhibiting an HDAC, e.g., HDAC6. The method involves administering to a patient in need thereof an effective amount of Formula I.

The present invention relates to compositions capable of modulating the activity of (e.g., inhibiting) HDACs, for instance HDAC6. The present invention also relates to the therapeutic use of such compounds.

One therapeutic use of the compounds of the present invention is to treat proliferative diseases or disorders such as cancer. Cancer can be understood as abnormal or unregulated cell growth within a patient and can include but is not limited to lung cancer, ovarian cancer, breast cancer, prostate cancer, pancreatic cancer, hepatocellular cancer, renal cancer and leukemias such as acute myeloid leukemia and acute lymphoblastic leukemia. Additional cancer types include T-cell lymphoma (e.g., cutaneous T-cell lymphoma, peripheral T-cell lymphoma), and multiple myeloma.

One therapeutic use of the compounds of the present invention is to treat neurological diseases or disorders or neurodegeneration. Neurological disorders are understood as disorders of the nervous system (e.g., the brain and spinal cord). Neurological disorders or neurodegenerative diseases can include but are not limited to epilepsy, attention deficit disorder (ADD), Alzheimer's disease, Parkinson's Disease, Huntington's Disease, amyotrophic lateral sclerosis, spinal muscular atrophy, essential tremor, central nervous system trauma caused by tissue injury, oxidative stress-induced neuronal or axonal degeneration, and multiple sclerosis.

The general way of preparing target molecules of Formula (I) by using Intermediates 2p, 2q, 2r, 2s, 2t, and 2u is outlined in General Scheme 3. Reductive amination of the aldehyde of 2q with the amino group of 2p in the presence of an acid, e.g., acetic acid using a reducing agent, e.g., sodium cyanoborohydride ($NaBH_3CN$) in a solvent, e.g., dichloromethane (DCM) followed by protection of the resulting amine with a protecting group, e.g., benzyl chloroformate, in the presence of a base, e.g., potassium carbonate ($K_2CO_3$), provides Intermediate 2r. Selective deprotection of the tert-butoxycarbonyl (Boc) protecting group of Another therapeutic use of the compounds of the present invention is to treat neurodevelopmental disorders. Neurodevelopmental disorders can include, but are not limited to, Rett syndrome.

Another therapeutic use of the compounds of the present invention is also to treat inflammatory diseases or disorders. Inflammation can be understood as a host's response to an initial injury or infection. Symptoms of inflammation can include but are not limited to redness, swelling, pain, heat and loss of function. Inflammation may be caused by the upregulation of pro-inflammatory cytokines such as IL-10, and increased expression of the FOXP3 transcription factor.

Another therapeutic use of the compounds of the present invention is also to treat autoimmune diseases or disorders. Autoimmune disorders are understood as disorders wherein a host's own immune system responds to tissues and substances occurring naturally in the host's body. Autoimmune diseases can include but are not limited to Rheumatoid arthritis, spondylitis arthritis, psoriatic arthritis, multiple sclerosis, systemic lupus erythematosus, inflammatory bowel disease, graft versus host disease, transplant rejection, fibrotic disease, Crohn's Disease, type-1 diabetes, Eczema, and psoriasis.

Another therapeutic use of the compounds of the present invention is also to treat infectious diseases or disorders. Infections or infectious diseases are caused by the invasion of a foreign pathogen. The infection may be caused by, for instance, a bacteria, a fungus, or virus. For example, a bacterial infection may be caused by a *E. coli.*

Yet another therapeutic use of the compounds of the present invention is also to treat metabolic diseases or disorders. Metabolic diseases can be characterized as abnormalities in the way that a subject stores energy. Metabolic disorders can include but are not limited to metabolic syndrome, diabetes, obesity, high blood pressure, and heart failure.

Yet another therapeutic use of the compounds of the present invention is also to treat hematologic disorders. Hematologic diseases primarily affect the blood. Hematologic disorders can include but are not limited to anemia, lymphoma, and leukemia.

Yet another therapeutic use of the compounds of the present invention is also to treat cardiovascular diseases or disorders. Cardiovascular diseases affect the heart and blood vessels of a patient. Exemplary conditions include but are not limited to cardiovascular stress, pressure overload, chronic ischemia, infarction-reperfusion injury, hypertension, atherosclerosis, peripheral artery disease, and heart failure.

The disclosed compound can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention relates to a pharmaceutical composition comprising a compound of Formulae I or II and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Without wishing to be bound by any particular theory, the compounds of the present invention can inhibit HDACs such as HDAC6 by interacting with the zinc ($Zn^{2+}$) ion in the protein's active site via the hydroxamic acid group bound to the aromatic ring of the compound. The binding can prevent the zinc ion from interacting with its natural substrates, thus inhibiting the enzyme.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The present invention includes a number of unique features and advantages compared with other inhibitors of HDAC enzymes, in particular HDAC6. For instance, the present invention features a unique class of small molecule therapeutic agents of Formulae I or II. The compounds were designed by using crystal structure information of HDAC ligand-protein complexes as well as advanced computational chemistry tools. These techniques led to the development of new chemical scaffolds that were iteratively refined to optimize key recognition features between the ligand and receptor known to be necessary for potency.

Definitions used in the following examples and elsewhere herein are:

$BH_3$: borane
DMSO: dimethylsulfoxide
EtOH: ethanol
$H_2SO_4$: sulfuric acid
KCl: potassium chloride
LiHMDS: lithium bis(trimethylsilyl)amide
CH2Cl2: methylene chloride, dichloromethane
CO: carbon monoxide
DIEA: diisopropylethylamine
DMF: N,N-dimethylformamide
EtOAc: ethyl acetate
H2O: water
HCl: hydrochloric acid
HATU: 1-[bis(dimethylamino)methylene]-1H-1,2,3-triazolo[4,5-b]pyridinium 3-oxid hexafluorophosphate
MeCN: acetonitrile
MeOH: methanol
NaHCO3: sodium bicarbonate
NaOH: sodium hydroxide
Pd(dppf)Cl$_2$.CH$_2$Cl$_2$: [1,1'-bis(diphenylphosphino)ferrocene]dichloro palladium(II)-dichloromethane adduct
pet. ether: petroleum ether
TFA: trifluoroacetic acid
THF: tetrahydrofuran Example 1—Preparation of N-hydroxy-3,4,5,6-tetrahydro-2H-benzo[b][1,5]oxazocine-9-carboxamide

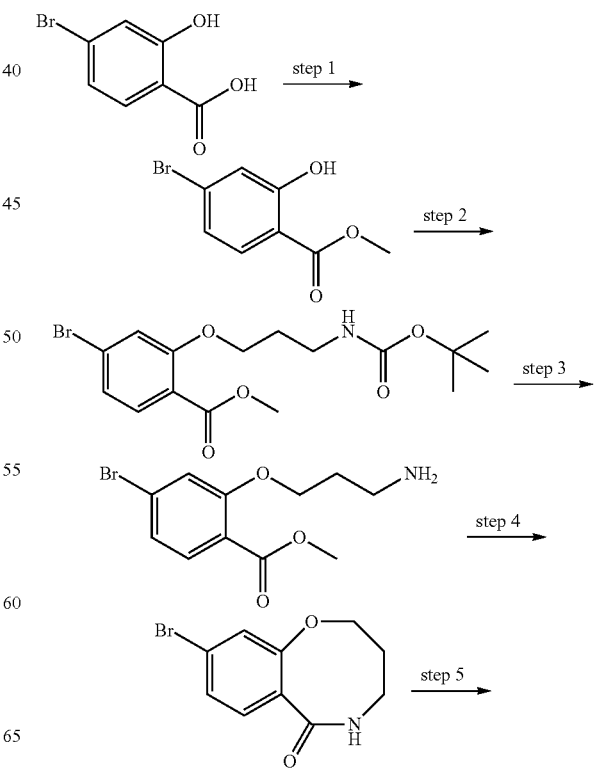

29

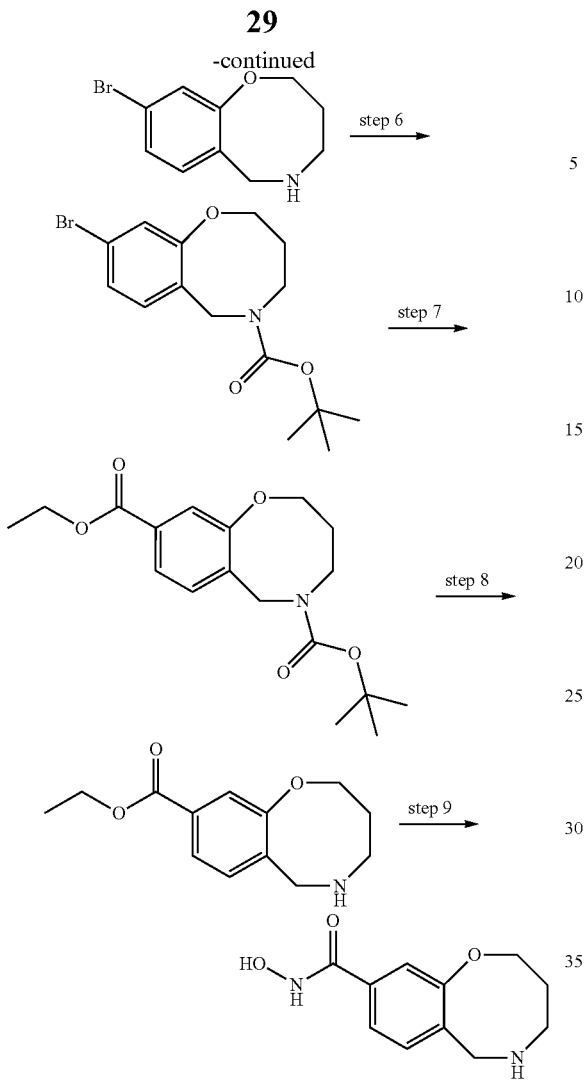

Step-1: Methyl 4-bromo-2-hydroxybenzoate

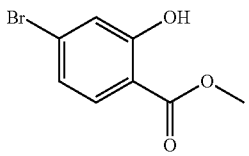

4-Bromo-2-hydroxybenzoic acid (10.0 g, 46.08 mmol, 1.0 equiv) and MeOH (50 mL) were placed in a 250-mL round-bottom flask. This was followed by the addition of sulfuric acid (20 mL) dropwise with stirring at 0° C. The resulting solution was stirred for 16 h at 65° C. in an oil bath, then concentrated under vacuum. The residue was dissolved in EtOAc (300 mL) and washed with $H_2O$ (3×100 mL) and aq. 2N $NaHCO_3$ (3×100 mL). The organic layer was dried over anhydrous sodium sulfate, filtered, concentrated, and purified by silica gel chromatography (EtOAc/pet. ether, 1:20) to afford methyl 4-bromo-2-hydroxybenzoate as a light yellow solid (7.80 g, 73% yield). MS: (ES, m/z): 231 [M+H]+.

Step-2: Methyl 4-bromo-2-(3-(tert-butoxycarbonylamino)propoxy)benzoate

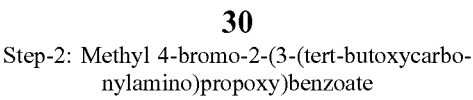

Methyl 4-bromo-2-hydroxybenzoate (3.00 g, 12.98 mmol, 1.0 equiv) in propan-2-one (15 mL), potassium carbonate (5.40 g, 39.07 mmol, 3.0 equiv) and tert-butyl N-(3-bromopropyl)carbamate (3.7 g, 15.54 mmol, 1.20 equiv) were place in a 100-mL round-bottom flask. The resulting mixture was stirred for 16 h at 60° C. in an oil bath, then concentrated under vacuum. The residue was dissolved in EtOAc (200 mL) and washed with $H_2O$ (3×100 mL). The organic layer was dried over anhydrous sodium sulfate, filtered, and concentrated to afford methyl 4-bromo-2-(3-(tert-butoxycarbonylamino)propoxy)benzoate as a light yellow oil (5.89 g). This material was used without further purification. MS: (ES, m/z): 388 [M+H]+.

Step-3: Methyl 2-(3-aminopropoxy)-4-bromobenzoate

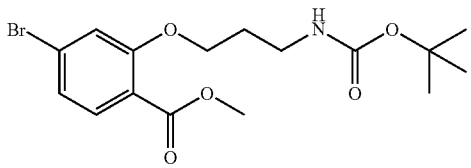 [SMILES: COC(=O)c1ccc(Br)cc1OCCCNC(=O)OC(C)(C)C]

Methyl 4-bromo-2-(3-(tert-butoxycarbonylamino) propoxy)benzoate (3.0 g, 7.73 mmol) and dichloromethane (10 mL) were placed in a 100-mL round-bottom flask. This was followed by the addition of trifluoroacetic acid (10 mL) dropwise with stirring at 0° C. The resulting solution was stirred for 3 h at room temperature, then concentrated under vacuum. The residue was dissolved in $H_2O$ (150 mL) and the pH of the solution was adjusted to 8 with aq. 4N NaOH. The resulting solution was extracted with EtOAc (3×100 mL). The organic layer was dried over anhydrous sodium sulfate, filtered, and concentrated under vacuum to afford methyl 2-(3-aminopropoxy)-4-bromobenzoate as a yellow oil (1.57 g, 71% yield). MS: (ES, m/z): 288 [M+H]+.

Step-4: 9-Bromo-2,3,4,5-tetrahydro-6H-benzo[b][1,5]oxazocin-6-one

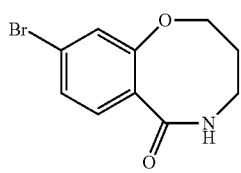 [SMILES: O=C1NCCCOc2cc(Br)ccc21]

Methyl 2-(3-aminopropoxy)-4-bromobenzoate (1.57 g, 5.45 mmol, 1.0 equiv) and THF (1.5 L) were placed in a 3-L 3-necked round-bottom flask that has been purged and maintained with an inert atmosphere of nitrogen. This was followed by the addition of a solution of LiHMDS (1M, 27 mL, 5.0 equiv) in THF (31 mL) dropwise with stirring at −5° C. The resulting solution was stirred for 16 h at room temperature. The reaction was then quenched by the addition of ethanol (30 mL) and concentrated under vacuum. The residue was dissolved in EtOAc (300 mL) and washed with H$_2$O (3×100 mL). The organic layer was dried over anhydrous sodium sulfate, filtered, concentrated, and purified by silica gel chromatography (MeOH/CH$_2$Cl$_2$, 1:20) to afford 9-bromo-2,3,4,5-tetrahydro-6H-benzo[b][1,5]oxazocin-6-one as a red solid (300 mg, 21% yield). MS: (ES, m/z): 256 [M+H]$^+$.

Step-5: 9-Bromo-3,4,5,6-tetrahydro-2H-benzo[b][1,5]oxazocine

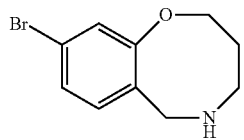 [SMILES: Brc1ccc2c(c1)OCCCNC2]

9-Bromo-2,3,4,5-tetrahydro-6H-benzo[b][1,5]oxazocin-6-one (300 mg, 1.17 mmol, 1.0 equiv) and THF (10 mL) were placed in a 50-mL round-bottom flask. This was followed by the addition of a solution of borane-tetrahydrofuran complex (1M, 11.80 mL) dropwise with stirring at 0° C. The resulting solution was stirred for 16 h at 60° C. in an oil bath. The reaction was then cooled to 0° C. and quenched by the addition of MeOH (5 mL) at 0° C. Then 6M HCl (3 mL) was added. The resulting solution was stirred for 16 h at room temperature. Then the pH of the reaction was adjusted to 8 with aq. 4N NaOH. The resulting mixture was concentrated under vacuum. The residue was dissolved in EtOAc (100 mL) and washed with H$_2$O (3×30 mL). The organic layer was dried over anhydrous sodium sulfate, filtered, and concentrated to afford 9-bromo-3,4,5,6-tetrahydro-2H-benzo[b][1,5]oxazocine as a light yellow solid (250 mg, 88% yield). MS: (ES, m/z): 242 [M+H]$^+$.

Step-6: tert-Butyl 9-bromo-3,4-dihydro-2H-benzo[b][1,5]oxazocine-5(6H)-carboxylate

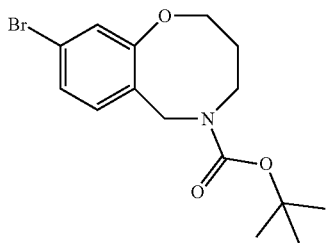 [SMILES: CC(C)(C)OC(=O)N1CCCOc2cc(Br)ccc2C1]

9-Bromo-3,4,5,6-tetrahydro-2H-benzo[b][1,5]oxazocine (140 mg, 0.58 mmol, 1.0 equiv), dichloromethane (5 mL), triethylamine (120 mg, 1.19 mmol, 2.0 equiv) and di-tert-butyl oxalate (260 mg, 1.29 mmol, 2.0 equiv) were placed in a 50-mL round-bottom flask. The resulting solution was stirred for 16 h at room temperature. The resulting mixture was concentrated and purified by silica gel chromatography (EtOAc/pet. ether, 1:3) to afford tert-butyl 9-bromo-3,4-dihydro-2H-benzo[b][1,5]oxazocine-5(6H)-carboxylate as a light yellow solid (130 mg, 66% yield). MS: (ES, m/z): 342 [M+H]$^+$.

Step-7: 5-(tert-Butyl) 9-ethyl-3,4-dihydro-2H-benzo[b][1,5]oxazocine-5,9(6H)-dicarboxylate

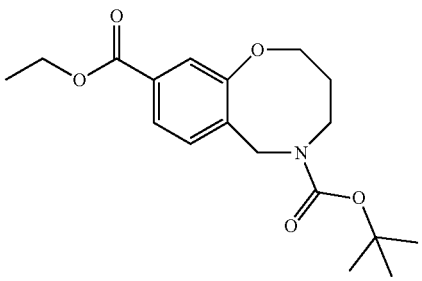 [SMILES: CCOC(=O)c1ccc2c(c1)OCCCN(C(=O)OC(C)(C)C)C2]

tert-Butyl 9-bromo-3,4-dihydro-2H-benzo[b][1,5]oxazocine-5(6H)-carboxylate (130 mg, 0.38 mmol, 1.0 equiv) in ethanol (10 mL), triethylamine (115 mg, 1.14 mmol, 3.0 equiv) and Pd(dppf)Cl$_2$.CH$_2$Cl$_2$ (27 mg, 0.04 mmol, 0.10 equiv) were placed in a 20-mL pressure tank reactor and CO(g) (50 atm) was introduced. The resulting mixture was stirred for 16 h at 120° C. in an oil bath and then concentrated under vacuum. The residue was dissolved in EtOAc (50 mL) and washed with H$_2$O (2×20 mL). The organic layer was dried over anhydrous sodium sulfate, filtered, concentrated, and purified by silica gel chromatography (EtOAc/pet. ether, 1:4) to afford 5-(tert-butyl) 9-ethyl-3,4-dihydro-2H-benzo[b][1,5]oxazocine-5,9(6H)-dicarboxylate as light yellow oil (90 mg, 71% yield). MS: (ES, m/z): 336 [M+H]$^+$.

Step-8: Ethyl 3,4,5,6-tetrahydro-2H-benzo[b][1,5]oxazocine-9-carboxylate

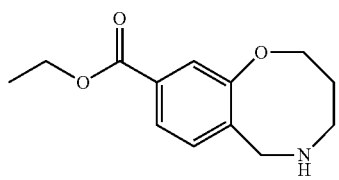 [SMILES: CCOC(=O)c1ccc2c(c1)OCCCNC2]

5-(tert-Butyl) 9-ethyl-3,4-dihydro-2H-benzo[b][1,5]oxazocine-5,9(6H)-dicarboxylate (90 mg, 0.27 mmol, 1.0 equiv) and dichloromethane (5 mL) were placed in a 50-mL round-bottom flask. This was followed by the addition of trifluoroacetic acid (5 mL) dropwise with stirring at 0° C. The resulting solution was stirred for 16 h at room temperature, then concentrated under vacuum. The residue was dissolved in H$_2$O (50 mL). The pH of the solution was adjusted to 8 with aq. 4N NaOH. The resulting solution was extracted with EtOAc (3×20 mL). The organic layer was dried over anhydrous sodium sulfate, filtered, and concentrated to afford ethyl 3,4,5,6-tetrahydro-2H-benzo[b][1,5]oxazocine-9-carboxylate as light yellow oil (60 mg, 95% yield). MS: (ES, m/z): 236 [M+H]$^+$.

Step-9: N-hydroxy-3,4,5,6-tetrahydro-2H-benzo[b][1,5]oxazocine-9-carboxamide

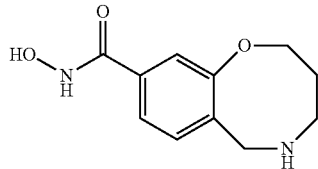 [SMILES: O=C(NO)c1ccc2c(c1)OCCCNC2]

Ethyl 3,4,5,6-tetrahydro-2H-benzo[b][1,5]oxazocine-9-carboxylate (60 mg, 0.26 mmol, 1.0 equiv) and THF/MeOH (4:1, 1.5 mL) were placed in a 8-mL vial. Then solutions of hydroxylamine (50% in water, 0.51 mL, 30 equiv) and aq. 1M NaOH (0.51 mL, 2.0 equiv) were added at the same time. The resulting solution was stirred for 2 h at room temperature. The crude product was purified by Prep-HPLC (Column: XBridge BEH C18 OBD Prep 5 μm 19×250 mm; Mobile Phase A:Water/0.05% TFA; Mobile Phase B: MeCN; Flow rate: 20 mL/min; Gradient: 2% B to 8% B in 6 min; Detector: UV 254, 220 nm). 1N HCl (0.26 mL, 1.0 equiv) was added to the product fractions and the mixture was lyophilized with 2N HCl (1 mL) to afford the hydrochloride salt of N-hydroxy-3,4,5,6-tetrahydro-2H-benzo[b][1,5]oxazocine-9-carboxamide as a off-white solid (23.7 mg, 36% yield). $^1$H-NMR (400 MHz, DMSO-$d_6$) δ (ppm): 11.35 (s, 1H), 9.42 (br s, 2H), 9.14 (br s, 1H), 7.61-7.54 (m, 3H), 4.17-4.15 (t, J=4.8 Hz, 4H), 3.13 (s, 2H), 1.82 (s, 2H). MS: (ES, m/z): 223 [M−HCl+H]$^+$.

Example 2—Preparation of N-hydroxy-5-(tetrahydro-2H-pyran-4-carbonyl)-3,4,5,6-tetrahydro-2H-benzo[b][1,5]oxazocine-9-carboxamide

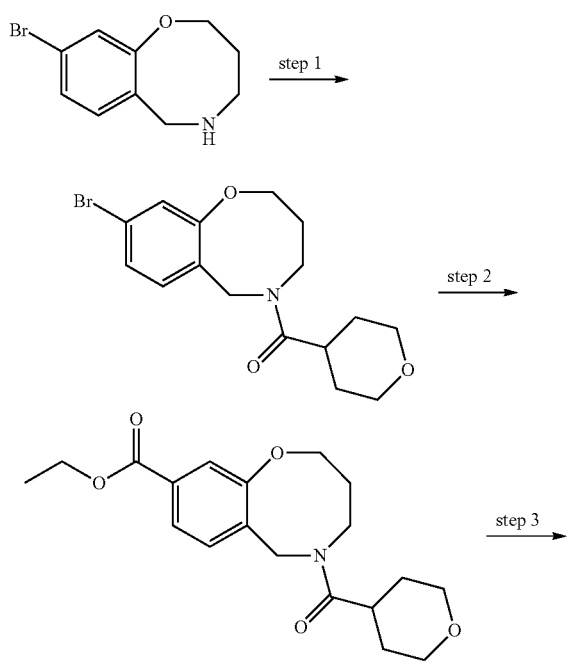

Step-1: 9-Bromo-3,4-dihydro-2H-benzo[b][1,5]oxazocin-5(6H)-yl)(tetrahydro-2H-pyran-4-yl)methanone

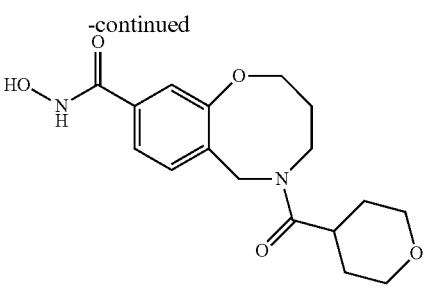

9-Bromo-3,4,5,6-tetrahydro-2H-benzo[b][1,5]oxazocine (250 mg, 1.03 mmol, 1.0 equiv) and DMF (3 mL) were placed in a 25-mL round-bottom flask. This was followed by the addition of oxane-4-carboxylic acid (162 mg, 1.24 mmol, 1.2 equiv), HATU (471 mg, 1.95 mmol, 1.2 equiv) and DIEA (402 mg, 3.11 mmol, 3.0 equiv) at 0° C. The resulting solution was stirred for 16 h at room temperature. The resulting solution was diluted with EtOAc (15 mL) and washed with H$_2$O (5×50 mL). The organic layer was dried over anhydrous sodium sulfate, filtered, concentrated, and purified by silica gel chromatography (MeOH/CH$_2$Cl$_2$, 1:25) to afford 9-bromo-3,4-dihydro-2H-benzo[b][1,5]oxazocin-5(6H)-yl)(tetrahydro-2H-pyran-4-yl)methanone as light yellow oil (200 mg, 55% yield). MS: (ES, m/z): 354 [M+H]$^+$.

Step-2: Ethyl 5-(tetrahydro-2H-pyran-4-carbonyl)-3,4,5,6-tetrahydro-2H-benzo[b][1,5]oxazocine-9-carboxylate

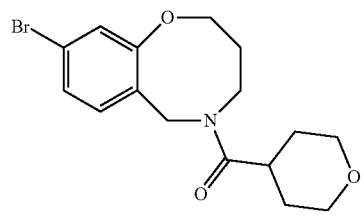 [SMILES: O=C(C1CCOCC1)N1CCCOc2cc(Br)ccc2C1]

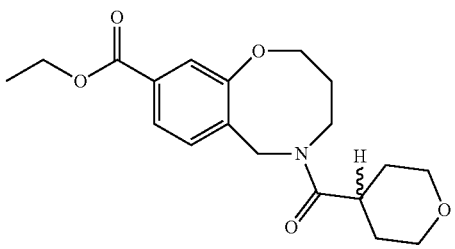 [SMILES: CCOC(=O)c1ccc2c(c1)OCCCN(C(=O)C1CCOCC1)C2]

9-Bromo-3,4-dihydro-2H-benzo[b][1,5]oxazocin-5(6H)-yl)(tetrahydro-2H-pyran-4-yl)methanone (170 mg, 0.48 mmol, 1.0 equiv) in EtOH (15 mL), triethylamine (242 mg, 2.39 mmol, 3.0 equiv) and Pd(dppf)Cl$_2$·CH$_2$Cl$_2$ (36 mg, 0.05 mmol, 0.10 equiv) were place in a 20-mL pressure tank reactor and CO(g) (50 atm) was introduced. The resulting mixture was stirred for 16 h at 120° C. in an oil bath. The resulting mixture was concentrated and purified by silica gel chromatography (MeOH/CH$_2$Cl$_2$, 1:25) to afford ethyl 5-(tetrahydro-2H-pyran-4-carbonyl)-3,4,5,6-tetrahydro-2H-benzo[b][1,5]oxazocine-9-carboxylate as light brown oil (160 mg, 96% yield). MS: (ES, m/z): 348 [M+H]$^+$.

Step-3: N-Hydroxy-5-(tetrahydro-2H-pyran-4-carbonyl)-3,4,5,6-tetrahydro-2H-benzo[b][1,5]oxazocine-9-carboxamide

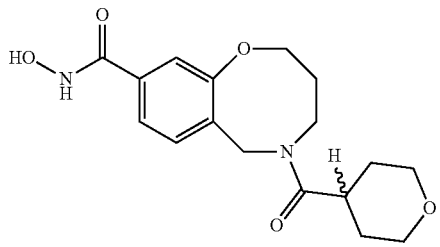 [SMILES: O=C(NO)c1ccc2c(c1)OCCCN(C(=O)C1CCOCC1)C2]

Ethyl 5-(tetrahydro-2H-pyran-4-carbonyl)-3,4,5,6-tetrahydro-2H-benzo[b][1,5]oxazocine-9-carboxylate (85 mg, 0.24 mmol, 1.0 equiv) and THF/MeOH (4:1, 1.5 mL) were placed in a 8-mL vial. Then solutions of hydroxylamine (50% in water, 0.48 mL, 30 equiv) and aq. 1N NaOH (0.49 mL, 2.0 equiv) were added at the same time. The resulting solution was stirred for 2 h at room temperature. The crude product was purified by Prep-HPLC (Column: XBridge C18 OBD Prep 5 μm 19×150 mm; Mobile Phase A:Water/0.1% Formic Acid; Mobile Phase B: MeCN; Flow rate: 25 mL/min; Gradient: 5% B to 43% B in 7 min; Detector: UV 254, 220 nm) to afford N-hydroxy-5-(tetrahydro-2H-pyran-4-carbonyl)-3,4,5,6-tetrahydro-2H-benzo[b][1,5]oxazocine-9-carboxamide as a pink solid (12.7 mg, 16% yield). $^1$H NMR (400 MHz, DMSO-d$_6$) δ (ppm): 11.10 (br s, 1H), 9.05 (br s, 1H), 7.53-7.39 (m, 3H), 4.71-4.48 (d, 2H), 4.16-4.03 (m, 2H), 3.82-3.67 (m, 4H), 3.37-3.30 (m, 2H), 3.00-2.76 (m, 1H), 1.76-1.72 (m, 2H), 1.61-1.25 (m, 4H). MS: (ES, m/z): 335 [M+H]$^+$.

Example 3 In Vitro Histone Deacetylase Assay

The enzymatic HDAC6 assay was performed using electrophoretic mobility shift assay. Full length human recombinant HDAC6 protein were expressed in baculoviral system and purified by affinity chromatography. The enzymatic reactions were assembled in 384 well plates in a total volume of 25 μL in a reaction buffer composing: 100 mM HEPES, pH7.5, 25 mM KCl, 0.1% bovine serum albumin, 0.01% Triton X-100, 1% DMSO (from compounds) 2 μM of the fluorescently labeled peptide substrate and enzyme. The enzyme was added at a final concentration of 1 nM. The peptide substrate RHKK(Ac)-NH2 was used. The compounds were tested at 12 concentrations spaced by 3× dilution intervals. Negative control samples (0%-inhibition in the absence of inhibitor) and positive control samples (100%-inhibition) were assembled in replicates of four in each assay plate. The reactions were incubated at 25° C. and quenched by the addition of 45 μL of termination buffer (100 mM HEPES, pH 7.5, 0.01% Triton X-100, 0.05% SDS).

The terminated assay plates were analyzed on LabChip® 3000 microfluidic electrophoresis instrument (Perkin Elmer/Caliper Life Sciences). The fluorescence intensity of the electrophoretically separated de-acetylated product and substrate peptide were measured. Activity in each sample was determined as the product to sum ratio (PSR): P/(S+P), where P is the peak height of the product peptide and S is the peak height of the substrate peptide. Percent inhibition (Pinh) was determined using the following equation:

$$\text{Pin}h=(\text{PSR}0\%-\text{PSR}inh)/(\text{PSR}0\%-\text{PSR}100\%)*100,$$

where PSRinh is the product sum ratio in the presence of inhibitor, PSR0% is the average product sum ration in the absence of inhibitor and PSR100% is the average product sum ratio in 100%-inhibition control samples. The IC50 values of inhibitors are determined by fitting the %-inhibition curves with 4 parameter dose-response model using XLfit 4 software.

As set forth in Table 2, below, IC$_{50}$ values are defined as follows: IC50≤0.1 μM (+++); IC50>0.1 μM and ≤0.5 μM (++); IC50>0.5 μM (+).

TABLE 1

The following compound was prepared by the method of Example 2.

| Structure | Found M + H | $^1$H-NMR (400 MHz, DMSO-d$_6$) δ (ppm) |
|---|---|---|
| (structure) | (ES, m/z): 349 [M + H]$^+$ | 11.16 (br s, 1H), 9.05 (br s, 1H), 7.49-7.44 (m, 3H), 4.56 (s, 2H), 4.17-4.14 (t, J = 5.6 Hz, 2H), 3.82-3.80 (t, J = 4 Hz, 2H), 3.60-3.55 (m, 2H), 3.40-3.36 (t J = 8.8 Hz, 2H), 1.97-1.94 (d, J = 14.4 Hz, 2H), 1.65 (s, 2H), 1.46-1.40 (m, 2H), 1.22 (s, 3H). |

TABLE 2

Inhibitory Concentration (IC50) Values for Representative Compounds against HDAC6.

| NAME | Activity Range |
|---|---|
| N-hydroxy-3,4,5,6-tetrahydro-2H-benzo[b][1,5]oxazocine-9-carboxamide | + |
| N-hydroxy-5-(tetrahydro-2H-pyran-4-carbonyl)-3,4,5,6-tetrahydro-2H-benzo[b][1,5]oxazocine-9-carboxamide | ++ |
| N-hydroxy-5-(4-methyltetrahydro-2H-pyran-4-carbonyl)-3,4,5,6-tetrahydro-2H-benzo[b][1,5]oxazocine-9-carboxamide | +++ |

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A compound of Formula IA-2:

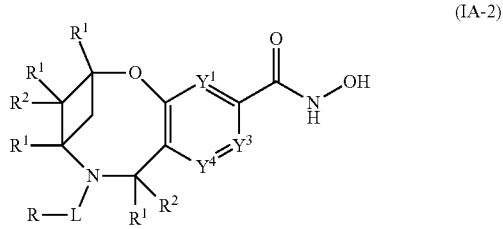

(IA-2)

or a pharmaceutically acceptable salt thereof, wherein
$Y^1$, $Y^3$, and $Y^4$ are each independently N or $CR^1$;
L is a bond, $-(CR^1R^2)_n-$, $-C(O)-$, $-C(O)O-$, $-C(O)NR^3-$, $-S(O)_2-$, $-S(O)_2NR^3-$, $-S(O)-$, $-S(O)NR^3-$, $-C(O)(CR^1R^2)_nO-$, or $-C(O)(CR^1R^2)_n-$;
R is independently, and at each occurrence, $-H$, $-C_1-C_6$alkyl, $-C_2-C_6$alkenyl, $-C_4-C_8$cycloalkenyl, $-C_2-C_6$alkynyl, $-C_3-C_8$cycloalkyl, $-C_5-C_{12}$spirocycle, heterocyclyl, spiroheterocyclyl, aryl, or heteroaryl containing 1-5 heteroatoms selected from N, S, P, or O, wherein each alkyl, alkenyl, cycloalkenyl, alkynyl, cycloalkyl, spirocycle, heterocyclyl, spiroheterocyclyl, aryl, or heteroaryl is optionally substituted with one or more $-OH$, halogen, oxo, $-NO_2$, $-CN$, $-R^1$, $-R^2$, $-OR^3$, $-NHR^3$, $-NR^3R^4$, $-S(O)_2NR^3R^4$, $-S(O)_2R^1$, $-C(O)R^1$, $-CO_2R^1$, $-NR^3S(O)_2R^1$, $-S(O)R^1$, $-S(O)NR^3R^4$, $-NR^3S(O)R^1$, heterocycle, aryl, or heteroaryl, with the proviso that when L is $-C(O)-$ the spiroheterocyclyl is not bound to L via a nitrogen atom;
$R^1$ and $R^2$ are independently, and at each occurrence, $-H$, $R^3$, $R^4$, $-C_1-C_6$alkyl, $-C_2-C_6$alkenyl, $-C_4-C_8$cycloalkenyl, $-C_2-C_6$alkynyl, $-C_3-C_8$cycloalkyl, heterocyclyl, aryl, heteroaryl containing 1-5 heteroatoms selected from N, S, P, or O, $-OH$, halogen, $-NO_2$, $-CN$, $-NHC_1-C_6$alkyl, $-N(C_1-C_6$alkyl$)_2$, $-S(O)_2N(C_1-C_6$alkyl$)_2$, $-N(C_1-C_6$alkyl$)S(O)_2R^5$, $-S(O)_2(C_1-C_6$alkyl$)$, $-(C_1-C_6$alkyl$)S(O)_2R^5$, $-C(O)$ $C_1-C_6$alkyl, $-CO_2C_1-C_6$alkyl, $-N(C_1-C_6$alkyl$)S(O)_2$ $C_1-C_6$alkyl, or $(CHR^5)_nNR^3R^4$, wherein each alkyl, alkenyl, cycloalkenyl, alkynyl, cycloalkyl, heterocyclyl, aryl, or heteroaryl is optionally substituted with one or more substituents selected from $-OH$, halogen, $-NO_2$, oxo, $-CN$, $-R^5$, $-OR^3$, $-NHR^3$, $-NR^3R^4$, $-S(O)_2N(R^3)_2$, $-S(O)_2R^5$, $-C(O)R^5$, $-CO_2R^5$, $-NR^3S(O)_2R^5$, $-S(O)R^5$, $-S(O)NR^3R^4$, $-NR^3S$ $(O)R^5$, heterocycle, aryl, or heteroaryl containing 1-5 heteroatoms selected from N, S, P, or O;
$R^3$ and $R^4$ are independently, and at each occurrence, $-H$, $-C_2-C_6$alkenyl, $-C_4-C_8$cycloalkenyl, $-C_2-C_6$alkynyl, $-C_3-C_8$cycloalkyl, heterocyclyl, aryl, heteroaryl containing 1-5 heteroatoms selected from N, S, P, or O, $-S(O)_2N(C_1-C_6$alkyl$)_2$, $-S(O)_2(C_1-C_6$alkyl$)$, $-(C_1-C_6$alkyl$)S(O)_2R^5$, $-C(O)C_1-C_6$alkyl, $-CO_2C_1-C_6$alkyl, or $-(CHR^5)_nN(C_1-C_6$alkyl$)_2$, wherein each alkyl, alkenyl, cycloalkenyl, alkynyl, cycloalkyl, heterocyclyl, aryl, and heteroaryl is optionally substituted with one or more substituents selected from $-OH$, halogen, $-NO_2$, oxo, $-CN$, $-R^5$, $-O(C_1-C_6)$alkyl, $-NH(C_1-C_6)$alkyl, $-N(C_1-C_6$alkyl$)_2$, $-S(O)_2N(C_1-C_6$alkyl$)_2$, $-S(O)_2NHC_1-C_6$alkyl, $-C(O)C_1-C_6$alkyl, $-CO_2C_1-C_6$alkyl, $-N(C_1-C_6$alkyl$)S(O)_2C_1-C_6$alkyl, $-S(O)R^5$, $-S(O)$ $N(C_1-C_6$alkyl$)_2$, $-N(C_1-C_6$alkyl$)S(O)R^5$, heterocycle, aryl, or heteroaryl containing 1-5 heteroatoms selected from N, S, P, or O;
$R^5$ is independently, and at each occurrence, $-H$, $-C_2-C_6$alkenyl, $-C_3-C_8$cycloalkenyl, $-C_2-C_6$alkynyl, $-C_3-C_8$cycloalkyl, heterocyclyl, aryl, heteroaryl, $-OH$, halogen, $-NO_2$, $-CN$, $-NHC_1-C_6$alkyl, $-N(C_1-C_6$alkyl$)_2$, $-S(O)_2NH(C_1-C_6$alkyl$)$, $-S(O)_2$ $N(C_1-C_6$alkyl$)_2$, $-S(O)_2C_1-C_6$alkyl, $-C(O)C_1-C_6$alkyl, $-CO_2C_1-C_6$alkyl, $-N(C_1-C_6$alkyl$)SO_2C_1-C_6$alkyl, $-S(O)(C_1-C_6$alkyl$)$, $-S(O)N(C_1-C_6$alkyl$)_2$, $-N(C_1-C_6$alkyl$)S(O)(C_1-C_6$alkyl$)$, or $-(CH_2)_nN(C_1-C_6$alkyl$)_2$; and
n is independently, and at each occurrence, an integer from 0 to 6.

2. A compound selected from the group consisting of:
N-hydroxy-5-phenyl-3,4,5,6-tetrahydro-2H-2,4-methanobenzo[b][1,5]oxazocine-9-carboxamide;
5-benzyl-N-hydroxy-3,4,5,6-tetrahydro-2H-2,4-methanobenzo[b][1,5]oxazocine-9-carboxamide;
5-benzoyl-N-hydroxy-3,4,5,6-tetrahydro-2H-2,4-methanobenzo[b][1,5]oxazocine-9-carboxamide;
5-(cyclohexanecarbonyl)-N-hydroxy-3,4,5,6-tetrahydro-2H-2,4-methanobenzo[b][1,5]oxazocine-9-carboxamide;
N-hydroxy-5-(tetrahydro-2H-pyran-4-carbonyl)-3,4,5,6-tetrahydro-2H-2,4-methanobenzo[b][1,5]oxazocine-9-carboxamide;
N-hydroxy-5-(phenylsulfonyl)-3,4,5,6-tetrahydro-2H-2,4-methanobenzo[b][1,5]oxazocine-9-carboxamide;
N9-hydroxy-N5-phenyl-3,4-dihydro-2H-2,4-methanobenzo[b][1,5]oxazocine-5,9(6H)-dicarboxamide;
N-hydroxy-5-(N-phenylsulfamoyl)-3,4,5,6-tetrahydro-2H-2,4-methanobenzo[b][1,5]oxazocine-9-carboxamide;
N-hydroxy-5-phenyl-3,4,5,6-tetrahydro-2H-2,4-methanobenzo[b][1,5]oxazocine-8-carboxamide;
5-benzyl-N-hydroxy-3,4,5,6-tetrahydro-2H-2,4-methanobenzo[b][1,5]oxazocine-8-carboxamide;
5-benzoyl-N-hydroxy-3,4,5,6-tetrahydro-2H-2,4-methanobenzo[b][1,5]oxazocine-8-carboxamide;

5-(cyclohexanecarbonyl)-N-hydroxy-3,4,5,6-tetrahydro-2H-2,4-methanobenzo[b][1,5]oxazocine-8-carboxamide;

N-hydroxy-5-(tetrahydro-2H-pyran-4-carbonyl)-3,4,5,6-tetrahydro-2H-2,4-methanobenzo[b][1,5]oxazocine-8-carboxamide;

N-hydroxy-5-(phenylsulfonyl)-3,4,5,6-tetrahydro-2H-2,4-methanobenzo[b][1,5]oxazocine-8-carboxamide;

N8-hydroxy-N5-phenyl-3,4-dihydro-2H-2,4-methanobenzo[b][1,5]oxazocine-5,8(6H)-dicarboxamide; and N-hydroxy-5-(N-phenylsulfamoyl)-3,4,5,6-tetrahydro-2H-2,4-methanobenzo[b][1,5]oxazocine-8-carboxamide, or a pharmaceutically acceptable salt thereof.

3. A pharmaceutical composition comprising a compound of claim 1 and a pharmaceutically acceptable carrier.

4. The compound of claim 1, wherein $Y^1$, $Y^3$, and $Y^4$ are each $CR^1$.

5. The compound of claim 4, wherein each $R_1$ and $R_2$ is H.

6. The compound of claim 5, wherein R is —$C_3$-$C_8$cycloalkyl, heterocyclyl, or aryl.

7. The compound of claim 6, wherein R is aryl.

8. The compound of claim 7, wherein R is phenyl.

9. The compound of claim 6, wherein R is heterocyclyl.

10. The compound of claim 6, wherein R is —$C_3$-$C_8$cycloalkyl.

11. The compound of claim 6, wherein L is a bond, —$CH_2$—, —C(O)—, —C(O)NH—, —$S(O)_2$—, or —$S(O)_2$NH—.

12. The compound of claim 11, wherein L is a bond.

13. The compound of claim 11, wherein L is —$CH_2$—.

14. The compound of claim 11, wherein L is —C(O)—.

15. The compound of claim 11, wherein L is —C(O)NH—.

16. The compound of claim 11, wherein L is —$S(O)_2$—.

17. The compound of claim 11, wherein L is —$S(O)_2$NH—.

18. A pharmaceutical composition comprising a compound of claim 2 and a pharmaceutically acceptable carrier.

* * * * *